US012662683B2

(12) United States Patent
Coles et al.

(10) Patent No.: US 12,662,683 B2
(45) Date of Patent: Jun. 23, 2026

(54) METHODS TO EVALUATE TRAITS

(71) Applicant: PIONEER HI-BRED INTERNATIONAL, INC., Johnston, IA (US)

(72) Inventors: Nathan David Coles, Johnston, IA (US); Jeffrey M Hegstad, Ankeny, IA (US); Jasdeep S Mutti, Johnston, IA (US)

(73) Assignee: PIONEER HI-BRED INTERNATIONAL, INC., Johnston, IA (US)

( * ) Notice: Subject to any disclaimer, the term of this patent is extended or adjusted under 35 U.S.C. 154(b) by 0 days.

(21) Appl. No.: 17/041,265

(22) PCT Filed: Mar. 26, 2019

(86) PCT No.: PCT/US2019/023970
§ 371 (c)(1),
(2) Date: Sep. 24, 2020

(87) PCT Pub. No.: WO2019/191023
PCT Pub. Date: Oct. 3, 2019

(65) Prior Publication Data
US 2021/0071192 A1 Mar. 11, 2021

Related U.S. Application Data

(60) Provisional application No. 62/650,746, filed on Mar. 30, 2018.

(51) Int. Cl.
*C12N 15/82* (2006.01)

(52) U.S. Cl.
CPC ....... *C12N 15/8261* (2013.01); *C12N 15/821* (2013.01); *C12N 15/8213* (2013.01)

(58) Field of Classification Search
None
See application file for complete search history.

(56) References Cited

U.S. PATENT DOCUMENTS

| | | | |
|---|---|---|---|
| 7,703,238 B2 * | 4/2010 | Deppermann | ........... A01H 5/10 |
| | | | 47/58.1 R |
| 10,233,456 B2 * | 3/2019 | Srivastava | ......... C12N 15/8213 |
| 2009/0031438 A1 * | 1/2009 | Kennard | ............ C12N 15/8254 |
| | | | 435/6.12 |
| 2013/0040826 A1 * | 2/2013 | Braun, III | ............ C12Q 1/6895 |
| | | | 506/2 |
| 2022/0361428 A1 | 11/2022 | Butruille et al. | |

OTHER PUBLICATIONS

Choi, Hae-Woon, et al. "Stability and inheritance of endosperm-specific expression of two transgenes in progeny from crossing independently transformed barley plants." Plant cell reports 28.8 (2009): 1265-1272. (Year: 2009).*

Bregitzer et al. (Crop science 43.1 (2003): 4-12). (Year: 2003).*

Belhaj et al. "Plant genome editing made easy: targeted mutagenesis in model and crop plants using the CRISPR/Cas system." Plant methods 9 (2013): 1-10. (Year: 2013).*

Li, et al.: "RNA-guided Cas9 as an in vivo desired-target mutator in maize", Plant Biotechnology Journal, 2017, vol. 15, No. 12, pp. 1566-1576.

International Search Report and Written Opinion for International Application No. PCT/US19/23970, Mailed Jun. 25, 2019.

International Preliminary Report on Patentability for International Application No. PCT/US2019/023970, mailed Oct. 15, 2020, 15 Pages.

* cited by examiner

*Primary Examiner* — Charles Logsdon

(57) ABSTRACT

The present disclosure provides methods for testing agronomic performance of transgenic traits and genome edits in plants and for accelerated selection of such plants. Methods evaluated include testing constructs for transgenic trait performance (T) using isolines. The methods comprise crossing events into different genetic backgrounds. Methods also comprise combining isoline data with F2:3 bulk data and developing breeding values across different genetic backgrounds for a higher level of confidence in selecting events.

8 Claims, 4 Drawing Sheets

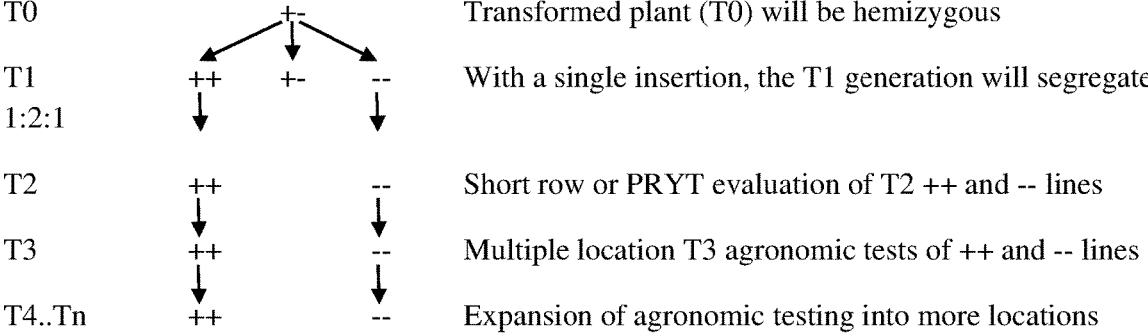

| T0 | | +- | | Transformed plant (T0) will be hemizygous |
|----|------|------|------|------|
| T1 | ++ | +- | -- | With a single insertion, the T1 generation will segregate |
| 1:2:1 | | | | |
| T2 | ++ | | -- | Short row or PRYT evaluation of T2 ++ and -- lines |
| T3 | ++ | | -- | Multiple location T3 agronomic tests of ++ and -- lines |
| T4..Tn | ++ | | -- | Expansion of agronomic testing into more locations |

FIG. 1

| Generation | Zygosity | | | Description |
|----|------|------|------|------|
| BCxF1 | | +- | | The BCxF1 plant will be heterozygous for the transgenic event |
| BCxF2:3 | ++ | +- | -- | The BCxF2:3 generation will segregate 1:2:1 for the event |
| BCxF3 | ++ | | -- | PRYT evaluation of transgene positive and negative sister lines |
| BCxF4..Fn | ++ | | -- | Expansion of agronomic testing into more locations |

FIG. 2

METHODS TO EVALUATE TRAITS

CROSS REFERENCE

This application is a 371 (National Stage) of PCT/US19/23970 filed Mar. 26, 2019, which claims the benefit of U.S. Provisional Application No. 62/650,746 filed Mar. 30, 2018, which are incorporated herein by reference in their entirety.

FIELD

The present disclosure relates to methods for testing agronomic performance of traits in plants.

BACKGROUND

A transgene is a segment of genetic material that can be introduced into another species using genetic engineering techniques. The introduced segment is able to produce a unique protein that confers a useful trait in field crops, such as herbicide tolerance, insect tolerance, or modifications to oil and meal quality. Genome editing with tools like CRISPR/Cas9 can also be used to create novel genetic diversity in a crop species enabling the development of unique trait mechanisms that do not exist or are not as readily accessible to breeders within the existing native germplasm pools.

Agronomic performance of transgenic traits and genome edited traits are evaluated for example in near-isogenic lines (isolines). Isolines are expected to have identical genetic backgrounds and differ for the presence or absence of a single gene of interest, e.g., trait of interest. Generally, for crop transgene and genome edit evaluation, the creation of isolines is a useful method to determine if any observed agronomic differences are correlated to a trait of interest.

There is a need in the field to develop methods for conducting agronomic field testing of novel transgenic and genome edited traits in soybean, corn and other crop plants to enable the acceleration and enhanced precision of advancement decisions.

SUMMARY

The present disclosure comprises methods to evaluate transgene by germplasm and genome edit by germplasm interactions in soybean, corn and other crop plants.

In an embodiment, a method for accelerated selection of a transgenic event includes crossing a plant line that is homozygous positive for a transgene with a diverse panel of plant lines that do not contain said transgene; crossing an isogenic transgene null with the same panel of plant lines that do not contain said transgene; collecting offspring of said crosses to produce transgene positive and transgene negative hybrids; phenotyping or genotyping the transgene positive hybrids and the transgene negative hybrids; assigning a breeding value to each transgenic event or a subset of the transgenic events in the transgene positive hybrids based on the phenotyping or the genotyping; and selecting the transgenic event based on the breeding value.

In an embodiment, a method for selecting a plant comprising an introduced genetic modification conferring a trait of interest, the method includes obtaining a F2 population of segregating plants from a F1 population resulting from crossing a plant line that contains the genetic modification to a second plant line that does not contain the genetic modification; generating a bulked pool of F2 population of plants that are homozygous positive for the genetic modification that is designated homozygous positive pool and generating a separate bulked pool of F2 plants that are homozygous negative for the genetic modification that is designated homozygous negative pool; phenotyping or genotyping a plurality of plants from the homozygous positive pool and the homozygous negative pool; assigning a breeding value to each plant or a subset of the plants in the bulked pool of plants that are homozygous positive for the genetic modification based on the phenotyping or the genotyping; and selecting the plant comprising the genetic modification based on the breeding value.

A method for accelerated selection of a genome edited plant line, the method includes crossing a genome edited plant line that comprises an introduced genome modification with a panel of plant lines that does not contain said genome modification; crossing an isogenic null with the same panel of plant lines that do not contain said genome modification; obtaining the hybrids of said crosses; phenotyping or genotyping the hybrids that are positive for the genome modification and the hybrids that are negative for the genome modification;

(e) assigning a breeding value to each genome edit plant or a subset of the genome edited plants in the genome edited positive hybrids based on the phenotyping or the genotyping; and (f) selecting the genome edit plant based on the breeding value In an embodiment, methods for testing and sorting transgenic constructs, transgenic events, or genome edited traits for trait performance (T) and trait by genotype interactions (TxG) are provided. In various aspects, the present disclosure provides methods for creating a population of plants with a transgenic event, the method comprising (a) crossing a plant line that contains a transgene of interest to a second plant line that does not contain said transgene; (b) collecting F1 offspring from said cross; (c) creating a F2 derived population of segregating individuals; (d) conducting an assay to determine which offspring from said population contain the transgene; (e) creating a bulked pool of plants that are homozygous positive for the transgenic event and a different bulked pool of plants that are homozygous negative for the transgenic event; (f) phenotyping the homozygous positive pool and the homozygous negative pool; and, (g) selecting the transgenic event producing a trait effect and agronomic phenotypes. In an aspect, the method further comprises after step (b) performing an assay to determine which of said offspring comprise the transgene. In an aspect, said F2 derived generation is a bi-parental population or a back-crossed population. In an aspect, the method further comprises growing the homozygous positive and homozygous negative plant pools in separate yield plots having similar environmental conditions. In an aspect, the method further comprises comparing agronomic characteristics of said homozygous positive pool and homozygous negative plant pool. In an aspect, the agronomic characteristics are selected from the group consisting of emergence, early vigor, growth, flowering time, flowering duration, height, maturity, and yield. In an aspect, the method further comprises setting a criterion for acceptable agronomic phenotype. In an aspect, the method further comprises determining whether the agronomic phenotypic differences between the homozygous positive and homozygous negative plant pools is of an acceptable level.

In various aspects, the present disclosure provides methods for creating a population of plants with a transgenic event, the method comprising: (a) crossing a plant line that contains a transgene of interest to a second plant line that does not contain said transgene; (b) collecting F1 offspring from said cross; (c) creating a double haploid (DH) plant population or a recombinant inbred line (RIL) plant population; (d) conducting an assay to determine which offspring from said population contain the transgene; (e) selecting a pool of plants that are homozygous positive for the transgenic event and a different pool of plants that are homozygous negative for the transgenic event; and, (f) selecting the transgenic event producing a trait effect and agronomic phenotypes. In an aspect, the method further comprises after step (b) performing an assay to determine which of said offspring comprise the transgene. In an aspect, the method further comprises growing the homozygous positive and homozygous negative plant pools in separate yield plots having similar environmental conditions. In an aspect, the method further comprises comparing agronomic characteristics of said homozygous positive pool and homozygous negative plant pool. In an aspect, the agronomic characteristics are selected from the group consisting of emergence, early vigor, growth, flowering time, flowering duration, height, maturity, and yield. In an aspect, whole genome molecular markers are used to characterize the double haploid plant population or the recombinant inbred line plant population. In an aspect, whole genome marker by transgene interactions is used to predict a win/loss and transgene breeding value of said transgene. In an aspect, the method further comprises setting a criterion for acceptable agronomic phenotype. In an aspect, the method further comprises determining whether the agronomic phenotypic differences between the homozygous positive and homozygous negative plant pools is of an acceptable level.

In various aspects, the present disclosure provides methods for creating a population of plants with a transgenic event, the method comprising: (a) crossing a plant line that is homozygous positive for a transgene with a diverse panel of plant lines that do not contain said transgene; (b) crossing an isogenic transgene null of (a) with the same panel of plant lines of (a) that do not contain said transgene; (c) collecting offspring of said crosses of (a) and (b); (d) pairing transgene positive and transgene negative hybrids; and, (e) selecting the transgenic event that produces an agronomic phenotype. In an aspect, the method further comprises growing the positive and negative hybrids in adjacent yield plots having similar environmental conditions. In an aspect, the method further comprises comparing agronomic characteristics of said positive pool and negative plant pool. In an aspect, the agronomic characteristics are selected from the group consisting of emergence, early vigor, growth, flowering time, flowering duration, height, maturity, and yield. In an aspect, whole genome molecular markers are used to characterize the hybrid plants. In an aspect, whole genome marker by transgene interactions is used to predict a win/loss and transgene breeding value of said transgene. In an aspect, the method further comprises setting a criterion for acceptable agronomic phenotype. In an aspect, the method further comprises determining whether the agronomic phenotypic differences between the homozygous positive and homozygous negative plant pools is of an acceptable level.

In various aspects, the present disclosure provides methods for creating a population of plants with a genome edit, the method comprising: (a) crossing a genome edited plant line with a plant line that does not contain said genome edit; (b) collecting F1 offspring from said cross; (c) creating an early generation bi-parental bulk plant population; (d) conducting an assay to determine which of said offspring contain the genome edited sequence of interest; (e) creating a bulked pool of plants that are homozygous positive for the genome edited sequence and a different bulked pool of plants that are homozygous negative for the genome edited sequence; (f) phenotyping the homozygous positive pool and the homozygous negative pool; and, (g) selecting the genome edited lines producing a trait effect and agronomic phenotypes. In an aspect, the method further comprises after step (b) performing an assay to determine which of said offspring comprises the transgene of interest. In an aspect, the early generation bi-parental bulk plant population is a F2, F3, F4 or back crossed population. In an aspect, the method further comprises growing the homozygous positive and homozygous negative plant pools in separate yield plots having similar environmental conditions. In an aspect, the method further comprises comparing agronomic characteristics of said homozygous positive pool and homozygous negative plant pool. In an aspect, the agronomic characteristics are selected from the group consisting of emergence, early vigor, growth, flowering time, flowering duration, height, maturity, and yield. In an aspect, the method further comprises setting a criterion for acceptable agronomic phenotype. In an aspect, the method further comprises determining whether the agronomic phenotypic differences between the homozygous positive and homozygous negative plant pools is of an acceptable level.

In various aspects, the present disclosure provides methods for determining the suitability of a genome edited line, the method comprising: (a) crossing a genome edited line with a plant that does not contain said genome edit; (b) collecting F1 offspring from said cross; (c) creating a double haploid (DH) plant population or a recombinant inbred line (RIL) plant population; (d) conducting an assay to determine which offspring from said population contain the genome edited sequence of interest; (e) selecting a plant pool that is homozygous positive for the genome edited sequence and a plant pool that is homozygous negative for the genome edited sequence; and (f) selecting the genome edited line producing a trait effect and agronomic phenotypes. In an aspect, the method further comprises after step (b) performing an assay to determine which of said offspring comprise the transgene. In an aspect, the method further comprises growing the homozygous positive and homozygous negative plant pools in separate yield plots having similar environmental conditions. In an aspect, the method further comprises comparing agronomic characteristics of said homozygous positive pool and homozygous negative plant pool. In an aspect, the agronomic characteristics are selected from the group consisting of emergence, early vigor, growth, flowering time, flowering duration, height, maturity, and yield. In an aspect, whole genome molecular markers are used to characterize the double haploid plant population or the recombinant inbred line plant population. In an aspect, whole genome marker by transgene interactions is used to predict a win/loss and transgene breeding value of said genome edit. In an aspect, the method further comprises setting a criterion for acceptable agronomic phenotype. In an aspect, the method further comprises determining whether the agronomic phenotypic differences between the homozygous positive and homozygous negative plant pools is of an acceptable level.

In various aspects, the present disclosure provides methods for determining the suitability of a genome edited plant line, the method comprising: (a) crossing a genome edited plant line with a plant that does not contain said genome edit; (b) crossing an isogenic null of (a) with the same panel of plant lines of (a) that do not contain said genome edit; (c) collecting offspring of said crosses of (a) and (b); (d) pairing genome edited positive and genome edited negative hybrids; and (e) selecting the genome edited line producing the most desirous agronomic phenotypes. In an aspect, the method further comprises growing the positive and negative hybrids in adjacent yield plots having similar environmental conditions. In an aspect, the method further comprises comparing agronomic characteristics of said positive pool and negative plant pool. In an aspect, the agronomic characteristics are selected from the group consisting of emergence, early vigor, growth, flowering time, flowering duration, height, maturity, and yield. In an aspect, whole genome molecular markers are used to characterize the hybrid plants. In an aspect, whole genome marker by transgene interactions is used to predict a win/loss and transgene breeding value of said transgene. In an aspect, the method further comprises setting a criterion for acceptable agronomic phenotype. In an aspect, the method further comprises determining whether the agronomic phenotypic differences between the homozygous positive and homozygous negative plant pools is of an acceptable level.

BRIEF DESCRIPTION OF THE DRAWINGS

FIG. 1 shows a representative process map for developing isolines of transgenic events for transgenic trait (T) agronomic field testing.

FIG. 2 shows a representative process map for developing homozygous lines from segregating backcross populations of transgenic events x elite varieties for TxG agronomic field testing.

DETAILED DESCRIPTION

Figure 3:
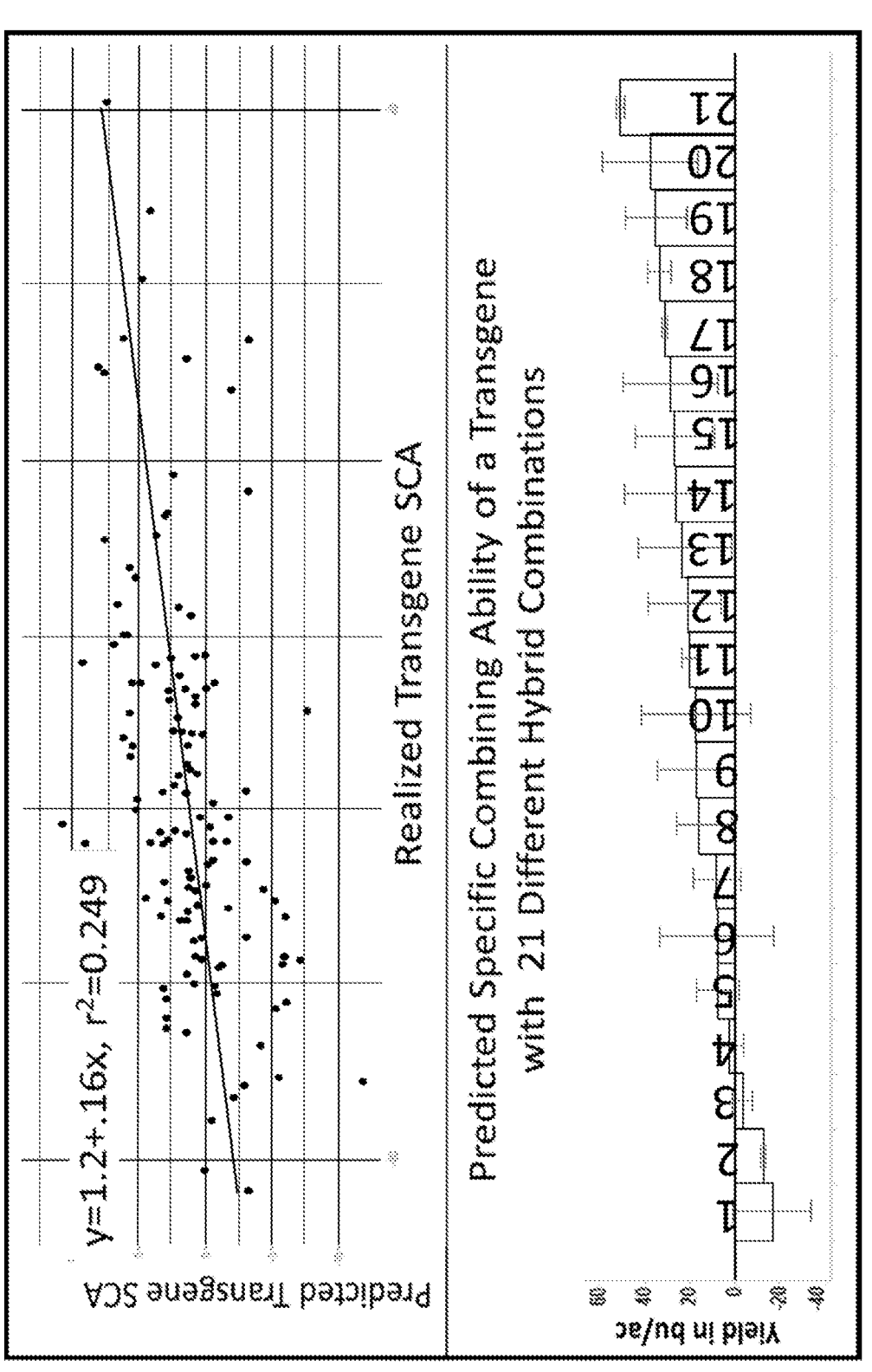
FIG. 3 shows differences (positive vs. negative) in emergence, maturity, and yield for two testing methods (isoline and F2:3 bulks) of three different genetic backgrounds.

The disclosures herein will be described more fully hereinafter with reference to the accompanying drawings, in which some, but not all possible aspects are shown. Indeed, disclosures may be embodied in many different forms and should not be construed as limited to the aspects set forth herein; rather, these aspects are provided so that this disclosure will satisfy applicable legal requirements.

In an embodiment, a method for selecting a transgenic event or a genome edited plant, the method includes obtaining F1 offspring from a cross resulting between a plant line that contains a transgene of interest or a genome modification to a second plant line that does not contain said transgene or said genome modification; creating a double haploid (DH) plant population or a recombinant inbred line (RIL) plant population based on the F1 offspring; conducting an assay to determine which offspring from said population contain the transgene or the genome modification; selecting a pool of plants that are homozygous positive for the transgenic event or the genome modification and a separate pool of plants that are homozygous negative for the transgenic event or the genome modification; and phenotyping or genotyping the homozygous positive pool and the homozygous negative pool; assigning a breeding value to each transgenic event or a subset of the transgenic events or each genome edited plant or a subset of the genome edited plants, in the bulked pool of plants that are homozygous positive for the transgenic event or the genome modification based on the phenotyping or genotyping; and selecting the transgenic event based on the breeding value.

In an embodiment, a method for accelerated selection of a genome edited plant, the method includes crossing a genome edited plant line that comprises an introduced genome modification with a plant line that does not contain said genome modification; collecting F1 offspring from said cross; creating an early generation bi-parental bulk plant population; conducting an assay to determine which of said offspring contain the genome modification of interest; creating a bulked pool of plants that are homozygous positive for the genome modification and a different bulked pool of plants that are homozygous negative for the genome modification; phenotyping or genotyping the homozygous positive pool and the homozygous negative pool; assigning a breeding value to each genome edited plant in the bulked pool of plants that are homozygous positive for the genome modification based on the phenotyping or the genotyping; and selecting the genome edit plant based on the breeding value.

In an embodiment, methods for testing agronomic performance of transgenic traits and genome edited traits in plants are provided. Methods for testing and sorting transgenic constructs, transgenic events, or genome edited traits for trait performance (T) and trait x genotype interactions (TxG) using different breeding techniques are also provided. Methods evaluated include testing trait performance (T) using isolines to understand initial trait effects. To understand trait x genotype interaction (TxG), different breeding techniques are used, such as comparing different filial generations (such as F1, F2, F2:3), comparing backcross generations (BC1Fn and BC2Fn), doubled haploids (DHs), recombinant inbred lines (RIL's) and association mapping. These methods may be used alone or in combination with each other. Combining the data from various methods disclosed herein allows for a greater confidence in selecting the best transgenic event or genome edited trait for advancement and potential commercialization.

Using isolines alone for agronomic testing may not be able to predict or infer how well the genome edit or transgene will perform in future commercial products, because early testing is often limited to only the isogenic variety, which may not be related to elite germplasm or current commercial products. Therefore, while isogenic lines provide some aspects of specific combining ability of the transgene or genome edit in that single background, they may not provide as good a representation of the general combining ability across germplasm, more generally. Further, unknown epigenetic effects such as somoclonal variation due to tissue culture procedures and variation due to transgene insertion, copy number, and position effects may also contribute towards the predictability or variability of product performance. To better understand the effects of transgenes and genome edits, evaluation of their performance in a wider genetic space is often conducted to understand potential trait x germplasm (TxG) interaction, but time consuming. This has been accomplished via accelerated trait introgression using backcrossing techniques, but the process is time consuming. In some aspects, even after backcrossing is completed, the inference space maybe limited to the newly created conversion germplasm. There are several challenges associated with the commercial advancement of transgenic constructs and genome edits into an elite breeding program. For example, it is often unknown what level of expression is needed for optimal trait performance in the final commercial varieties. It is therefore necessary to generate different constructs using promoters of different strength driving the same gene of interest or generate different genome edits of the same gene target to identify alleles with optimal trait expression.

For transgenic plants, each transformed cell produces a transgenic "event", which are grown into T0 plants using tissue culture techniques. Subsequent cycles of self-fertilization create the T1, T2, T3 . . . Tn event generations (see FIG. 1). Most current methods used to generate transgenic events in crop species create random insertions of the construct into the genome, often resulting in trait expression variability among different events from the same construct. More recently, CRISPR/CAS9 and other genome editing techniques have been utilized to introduce novel genetic variation into crop species for enhanced performance and targeted insertion of construct to specified location in the genome also known as site-specific integration.

Due to expression variability associated with transformation, it is useful to create multiple events from the same set of constructs to evaluate trait efficacy and agronomic performance. Random insertion of a transgene into the genome may induce unpredictable pleiotropic effects on traits of agronomic significance, such as plant growth, maturity, and/or final grain yield. It is therefore important to identify agronomic differences early in trait evaluation so that resources are not wasted on genetic variation that will eventually fail in the marketplace. The most commercially-successful transgenic events and new traits are those that are efficacious yet have little or no negative impact on agronomic traits and final yield.

Aspects of the present disclosure provide for methods for testing agronomic performance of transgenic traits and genome edited traits in plants.

One aspect of the present disclosure provides for transgene (T) by germplasm (G) testing utilizing an association mapping method. The association mapping method is an efficient way to test for TxG with minimal investment in germplasm development resources. It provides a quick estimate of the stability at either the construct or event level, depending on the method of hybrid seed production. Using this method, it is possible to develop an estimation set from association mapping with which TxG can be predicted across both tested and untested germplasm.

Another aspect of the present disclosure provides for developing isolines of transgenic events for transgenic trait (T) agronomic field testing (FIG. 1). To create transgenic isolines for each event, a transformed plant (T0) is allowed to self-fertilize to create segregating T1 seed. With a single gene insertion, T1 plants will segregate 1:2:1 (1 homozygous transgene positive: 2 heterozygous: 1 homozygous transgene negative). Testing for zygosity of T1 generation plants can be accomplished by using PCR assays to amplify the gene of interest or other components of the transgenic construct, such as the selectable marker. Selectable markers include, but are not limited to, (ALS), in particular the sulfonylurea-type herbicides (e.g., the acetolactate synthase (ALS) gene containing mutations leading to such resistance, in particular the S4 and/or Hra mutations), genes coding for resistance to herbicides that act to inhibit action of glutamine synthase, such as phosphinothricin or basta (e.g., the bar gene), glyphosate (e.g., the EPSPS gene and the GAT gene; see, for example, U.S. Publication No. 20040082770 and WO 03/092360) or other such genes known in the art. The bar gene encodes resistance to the herbicide basta, the nptII gene encodes resistance to the antibiotics kanamycin and geneticin, and the ALS-gene mutants encode resistance to the herbicide chlorsulfuron. Trait expression in the T1 generation can be determined by using RTPCR, ELISA, western, or other protein assays. The T1 homozygous positive plants and homozygous negative plants should be selected for seed increase. Heterozygous T1 plants can be discarded as they will continue to segregate in subsequent generations. Selected T1 plants should be harvested separately and T2 lines grown individually for seed increase in either single row evaluations, or plant row yield trials (PRYTs). Zygosity evaluation using PCR techniques and trait expression assays (and efficacy, if possible) should be verified in each individual T2 seed increase or PRYT row. Each individual T2 row should be bulk harvested separately to create T3 seed lots. The T3 seed lots should be tested for zygosity by analyzing an aliquot of at least 24 seed from each seed lot. If all 24 seed are positive, or all 24 seed are negative, there is a 95% probability that the seed lot is homozygous. T3 seed lots that are homozygous positive could then be bulked together and T3 seed lots that are homozygous negative could be bulked together for multiple location yield testing. Any T3 seed lot that has a mixture of positive and negative seeds should be discarded.

Another aspect of the present disclosure provides methods for developing homozygous lines from segregating backcross populations of transgenic events by elite varieties for TxG agronomic field testing (see FIG. 2). To analyze trait effects in different genetic backgrounds, the transgenic event is backcrossed to an elite variety. The BCxF1 plant will be heterozygous and the BCxF2:3 plants will segregate 1:2:1 (1 homozygous transgene positive: 2 heterozygous: 1 homozygous transgene negative). Testing for zygosity of BCxF2:3 plants can be accomplished by using PCR assays to amplify the gene of interest or other components of the transgenic construct. The homozygous transgene positive plants and homozygous transgene negative plants should be selected for seed increase. Heterozygous plants can be discarded as they will continue to segregate in subsequent generations. Selected BCxF2:3 plants should be harvested separately and lines grown individually for seed increase in either single row evaluations, or PRYTs. Zygosity evaluation using PCR techniques and trait expression assays (and efficacy, if possible) should be verified in each individual BCxF3 seed increase row. Each individual BCxF3 row should be bulk harvested separately to create BCxF4 seed lots. The BCxF4 seed lots should be tested for zygosity by analyzing an aliquot of at least 24 seeds from each seed lot. If all 24 seeds are positive, or all 24 seeds are negative, there is greater than 95% probability that the seed lot is homozygous. Individual lines that are verified to be homozygous (positive or null) can be advanced into multiple location TxG yield trials.

The methods and composition of the present disclosure may be used in any plant species, including, but not limited to, monocots and dicot crop specie. Examples of plant species of interest include, but are not limited to, corn (*Zea mays*), *Brassica* sp. (e.g., *B. napus, B. rapa, B. juncea*), particularly those *Brassica* species useful as sources of seed oil, rice (*Oryza sativa*), sorghum (*Sorghum bicolor, Sorghum vulgare*), sunflower (*Helianthus annuus*), wheat (*Triticum aestivum*), and soybean (*Glycine max*). Optimally, plants of the present disclosure are crop plants (for example, corn, alfalfa, sunflower, *Brassica*, soybean, cotton, safflower, peanut, *sorghum*, wheat, millet, tobacco, etc.), more optimally corn and soybean plants.

Methods to Improve Plant Traits and Characteristics

The present disclosure provides novel methods for producing plants with a transgenic event or producing plants with a genome edit. The disclosed methods can further comprise polynucleotides that provide for improved traits and characteristics.

As used herein, "trait" refers to a physiological, morphological, biochemical, or physical characteristic of a plant or particular plant material or cell. In some instances, this characteristic is visible to the human eye, such as seed or plant size, or can be measured by biochemical techniques, such as detecting the protein, starch, or oil content of seed or leaves, or by observation of a metabolic or physiological process, e.g. by measuring uptake of carbon dioxide, or by the observation of the expression level of a gene or genes, e.g., by employing Northern analysis, RT-PCR, microarray gene expression assays, or reporter gene expression systems, or by agricultural observations such as stress tolerance, yield, or pathogen tolerance. An "enhanced trait" of the present disclosure includes improved or enhanced emergence and early vigor, enhanced water use efficiency or drought tolerance, osmotic stress tolerance, high salinity stress tolerance, heat stress tolerance, enhanced cold tolerance, including cold germination tolerance, increased yield, enhanced nitrogen use efficiency, early plant growth and development, late plant growth and development, enhanced seed protein, and enhanced seed oil production.

Any polynucleotide of interest can be used in the methods of the disclosure. Various changes in phenotype are of interest including modifying the fatty acid composition in a plant, altering the amino acid content, starch content, or carbohydrate content of a plant, altering a plant's pathogen defense mechanism, affecting kernel size, sucrose loading, and the like. The gene of interest may also be involved in regulating the influx of nutrients, and in regulating expression of phytate genes particularly to lower phytate levels in the seed. These results can be achieved by providing expression of heterologous products or increased expression of endogenous products in plants. Alternatively, the results can be achieved by providing for a reduction of expression of one or more endogenous products, particularly enzymes or cofactors in the plant. These changes result in a change in phenotype of the transformed or genome edited plant.

More specific categories of transgenes may be used in the methods of the disclosure, for example, include genes encoding important traits for agronomics, insect resistance, disease resistance, herbicide resistance, sterility, grain characteristics, and commercial products. Genes of interest include, generally, those involved in oil, starch, carbohydrate, or nutrient metabolism as well as those affecting kernel size, sucrose loading, and the like.

The polynucleotides introduced into a plant by the disclosed methods can be operably linked to a suitable promoter. "Promoter" means a region of DNA that is upstream from the start of transcription and is involved in recognition and binding of RNA polymerase and other proteins to initiate transcription, either including or not including the 5' UTR. A "plant promoter" is a promoter capable of initiating transcription in plant cells whether or not its origin is a plant cell. Tissue specific, tissue preferred, cell type specific, and inducible promoters constitute the class of "non-constitutive" promoters. A "constitutive" promoter is a promoter which is active under most conditions. "Antisense orientation" includes reference to a polynucleotide sequence that is operably linked to a promoter in an orientation where the antisense strand is transcribed. The antisense strand is sufficiently complementary to an endogenous transcription product such that translation of the endogenous transcription product is often inhibited. "Operably linked" refers to the association of two or more nucleic acid fragments on a single nucleic acid fragment so that the function of one is affected by the other. For example, a promoter is operably linked with a coding sequence when it is capable of affecting the expression of that coding sequence (i.e., that the coding sequence is under the transcriptional control of the promoter). Coding sequences can be operably linked to regulatory sequences in sense or antisense orientation.

Agronomically important traits such as oil, starch, and protein content can be genetically altered in addition to using traditional breeding methods. Modifications include increasing content of oleic acid, saturated and unsaturated oils, increasing levels of lysine and sulfur, providing essential amino acids, and also modification of starch. Hordothionin protein modifications are described in U.S. Pat. Nos. 5,703,049, 5,885,801, 5,885,802, and 5,990,389, herein incorporated by reference. Another example is lysine and/or sulfur rich seed protein encoded by the soybean 2S albumin described in U.S. Pat. No. 5,850,016, and the chymotrypsin inhibitor from barley, described in Williamson et al. (1987) *Eur. J. Biochem.* 165:99-106, the disclosures of which are herein incorporated by reference.

Insect resistance genes may encode resistance to pests that have great yield drag such as rootworm, cutworm, European Corn Borer, and the like. Such genes include, for example, *Bacillus thuringiensis* toxic protein genes (U.S. Pat. Nos. 5,366,892; 5,747,450; 5,736,514; 5,723,756; 5,593,881; and Geiser et al. (1986) *Gene* 48:109); and, the like. Genes encoding disease resistance traits include detoxification genes, such as against fumonosin (U.S. Pat. No. 5,792,931); avirulence (avr) and disease resistance (R) genes (Jones et al. (1994) *Science* 266:789; Martin et al. (1993) *Science* 262:1432; and Mindrinos et al. (1994) *Cell* 78:1089); and the like.

Herbicide resistance traits may include genes coding for resistance to herbicides that act to inhibit the action of acetolactate synthase (ALS), in particular the sulfonylurea-type herbicides (e.g., the acetolactate synthase (ALS) gene containing mutations leading to such resistance, in particular the S4 and/or Hra mutations), genes coding for resistance to herbicides that act to inhibit action of glutamine synthase, such as phosphinothricin or basta (e.g., the bar gene), glyphosate (e.g., the EPSPS gene and the GAT gene; see, for example, U.S. Publication No. 20040082770 and WO 03/092360) or other such genes known in the art. The bar gene encodes resistance to the herbicide basta, the nptII gene encodes resistance to the antibiotics kanamycin and geneticin, and the ALS-gene mutants encode resistance to the herbicide chlorsulfuron.

Sterility genes can also be encoded in an expression cassette and provide an alternative to physical detasseling. Examples of genes used in such ways include male tissue-preferred genes and genes with male sterility phenotypes such as QM, described in U.S. Pat. No. 5,583,210. Other genes include kinases and those encoding compounds toxic to either male or female gametophytic development.

The quality of grain is reflected in traits such as levels and types of oils, saturated and unsaturated, quality and quantity of essential amino acids, and levels of cellulose. In corn, modified hordothionin proteins are described in U.S. Pat. Nos. 5,703,049, 5,885,801, 5,885,802, and 5,990,389.

In an aspect, further agronomic traits of interest that can be introduced into plants, such traits as increased yield or other trait that provides increased plant value, including, for example, improved seed quality. Of particular interest are traits that provide improved or enhanced water use efficiency or drought tolerance, osmotic stress tolerance, high salinity stress tolerance, heat stress tolerance, enhanced cold tolerance, including cold germination tolerance, increased yield, enhanced nitrogen use efficiency, early plant growth and development, late plant growth and development, enhanced seed protein, and enhanced seed oil production.

Many agronomic traits can affect grain yield, including without limitation, plant height, pod number, pod position on the plant, number of internodes, incidence of pod shatter, grain size, efficiency of nodulation and nitrogen fixation, efficiency of nutrient assimilation, resistance to biotic and abiotic stress, carbon assimilation, plant architecture, resistance to lodging, percent seed germination, seedling vigor, and juvenile traits. Other traits that can affect yield include, efficiency of germination (including germination in stressed conditions), growth rate (including growth rate in stressed conditions), ear number, seed number per ear, seed size, composition of seed (starch, oil, protein) and characteristics of seed fill. Also of interest is the generation of transgenic plants that demonstrate desirable phenotypic properties that may or may not confer an increase in overall plant yield. Such properties include enhanced plant morphology, plant physiology or improved components of the mature seed harvested from the transgenic plant.

"Increased yield" of a transgenic plant or genome edited plant of the present disclosure may be evidenced and measured in a number of ways, including test weight, seed number per plant, seed weight, seed number per unit area (i.e. seeds, or weight of seeds, per acre), bushels per acre, tons per acre, kilo per hectare. For example, maize yield may be measured as production of shelled corn kernels per unit of production area, e.g. in bushels per acre or metric tons per hectare, often reported on a moisture adjusted basis, e.g., at 15.5% moisture. Increased yield may result from improved utilization of key biochemical compounds, such as nitrogen, phosphorous and carbohydrate, or from improved tolerance to environmental stresses, such as cold, heat, drought, salt, and attack by pests or pathogens. Trait-enhancing recombinant DNA may also be used to provide transgenic plants having improved growth and development, and ultimately increased yield, as the result of modified expression of plant growth regulators or modification of cell cycle or photosynthesis pathways.

Many agronomic traits can affect "yield", including without limitation, plant height, pod number, pod position on the plant, number of internodes, incidence of pod shatter, grain size, efficiency of nodulation and nitrogen fixation, efficiency of nutrient assimilation, resistance to biotic and abiotic stress, carbon assimilation, plant architecture, resistance to lodging, percent seed germination, seedling vigor, and juvenile traits. Other traits that can affect yield include, efficiency of germination (including germination in stressed conditions), growth rate (including growth rate in stressed conditions), ear number, seed number per ear, seed size, composition of seed (starch, oil, protein) and characteristics of seed fill. Also of interest is the generation of transgenic plants that demonstrate desirable phenotypic properties that may or may not confer an increase in overall plant yield. Such properties include enhanced plant morphology, plant physiology or improved components of the mature seed harvested from the transgenic plant.

Methods to Introduce Targeted, Site-Specific Genome Edits into Plants

In an aspect, the disclosed methods can be used to introduce into plants polynucleotides useful to target a specific site for modification in the genome of a plant. Site specific modifications that can be introduced with the disclosed methods and compositions include those produced using any method for introducing site specific modification, including, but not limited to, through the use of gene repair oligonucleotides (e.g. US Publication 2013/0019349), or through the use of double-stranded break technologies such as TALENs, meganucleases, zinc finger nucleases, CRISPR-Cas, and the like. For example, the disclosed methods and compositions can be used to introduce a CRISPR-Cas system into plants, for the purpose of genome modification of a target sequence in the genome of a plant or plant cell, for selecting plants, for deleting a base or a sequence, for gene editing, and for inserting a polynucleotide of interest into the genome of a plant. Thus, the disclosed methods and compositions can be used together with a CRISPR-Cas system to provide for an effective system for modifying or altering target sites and nucleotides of interest within the genome of a plant, plant cell or seed.

In an aspect, the present disclosure comprises methods and compositions for producing a transgenic plant or a genome edited plant, wherein the method comprises introducing a polynucleotide of interest into a target site in the genome of a plant cell. In an aspect, the Cas endonuclease gene is a plant optimized Cas9 endonuclease, wherein the plant optimized Cas9 endonuclease is capable of binding to and creating a double strand break in a genomic target sequence the plant genome.

The Cas endonuclease is guided by the guide nucleotide to recognize and optionally introduce a double strand break at a specific target site into the genome of a cell. The CRISPR-Cas system provides for an effective system for modifying target sites within the genome of a plant, plant cell or seed. Further provided are methods and compositions employing a guide polynucleotide/Cas endonuclease system to provide an effective system for modifying target sites within the genome of a cell and for editing a nucleotide sequence in the genome of a cell. Once a genomic target site is identified, a variety of methods can be employed to further modify the target sites such that they contain a variety of polynucleotides of interest. The disclosed compositions and methods can be used to introduce a CRISPR-Cas system for editing a nucleotide sequence in the genome of a cell. The nucleotide sequence to be edited (the nucleotide sequence of interest) can be located within or outside a target site that is recognized by a Cas endonuclease.

CRISPR loci (Clustered Regularly Interspaced Short Palindromic Repeats) (also known as SPIDRs-SPacer Interspersed Direct Repeats) constitute a family of recently described DNA loci. CRISPR loci consist of short and highly conserved DNA repeats (typically 24 to 40 bp, repeated from 1 to 140 times—also referred to as CRISPR-repeats) which are partially palindromic. The repeated sequences (usually specific to a species) are interspaced by variable sequences of constant length (typically 20 to 58 by depending on the CRISPR locus (WO2007/025097 published Mar. 1, 2007). Cas gene includes a gene that is generally coupled, associated or close to or in the vicinity of flanking CRISPR loci. The terms "Cas gene" and "CRISPR-associated (Cas) gene" are used interchangeably herein. A comprehensive review of the Cas protein family is presented in Haft et al. (2005) Computational Biology, PLoS Comput Biol 1 (6): e60. doi:10.1371/journal.pcbi.0010060.

In addition to the four initially described gene families, an additional 41 CRISPR-associated (Cas) gene families have been described in WO/2015/026883, which is incorporated herein by reference. This reference shows that CRISPR systems belong to different classes, with different repeat patterns, sets of genes, and species ranges. The number of Cas genes at a given CRISPR locus can vary between species. Cas endonuclease relates to a Cas protein encoded by a Cas gene, wherein the Cas protein is capable of introducing a double strand break into a DNA target sequence. The Cas endonuclease is guided by the guide polynucleotide to recognize and optionally introduce a double strand break at a specific target site into the genome of a cell. As used herein, the term "guide polynucleotide/Cas endonuclease system" includes a complex of a Cas endonuclease and a guide polynucleotide that is capable of introducing a double strand break into a DNA target sequence. The Cas endonuclease unwinds the DNA duplex in close proximity of the genomic target site and cleaves both DNA strands upon recognition of a target sequence by a guide nucleotide, but only if the correct protospacer-adjacent motif (PAM) is approximately oriented at the 3' end of the target sequence (see FIG. 2A and FIG. 2B of WO/2015/026883, published Feb. 26, 2015).

The terms "functional fragment," "fragment that is functionally equivalent," and "functionally equivalent fragment" are used interchangeably herein. These terms refer to a portion or subsequence of the Cas endonuclease sequence of the present disclosure in which the ability to create a double-strand break is retained. The terms "functional variant," "variant that is functionally equivalent" and "functionally equivalent variant" are used interchangeably herein. These terms refer to a variant of the Cas endonuclease of the present disclosure in which the ability to create a double-strand break is retained. Fragments and variants can be obtained via methods such as site-directed mutagenesis and synthetic construction.

In an aspect, the Cas endonuclease gene is a *Streptococcus pyogenes* Cas9 gene that can recognize any genomic sequence of the form N(12-30)NGG can in principle be targeted.

Endonucleases also include meganucleases, also known as homing endonucleases (HEases), which like restriction endonucleases, bind and cut at a specific recognition site, however the recognition sites for meganucleases are typically longer, about 18 bp or more. TAL effector nucleases are a new class of sequence-specific nucleases that can be used to make double-strand breaks at specific target sequences in the genome of a plant or other organism. (Miller, et al. (2011) Nature Biotechnology 29:143-148). Zinc finger nucleases (ZFNs) are engineered double-strand break inducing agents comprised of a zinc finger DNA binding domain and a double-strand-break-inducing agent domain. Recognition site specificity is conferred by the zinc finger domain, which typically comprising two, three, or four zinc fingers, for example having a C2H2 structure, however other zinc finger structures are known and have been engineered. Zinc finger domains are amenable for designing polypeptides which specifically bind a selected polynucleotide recognition sequence. ZFNs include an engineered DNA-binding zinc finger domain linked to a nonspecific endonuclease domain, for example nuclease domain from a Type Ms endonuclease such as Fokl. Additional functionalities can be fused to the zinc-finger binding domain, including transcriptional activator domains, transcription repressor domains, and methylases. In some examples, dimerization of nuclease domain is required for cleavage activity. Each zinc finger recognizes three consecutive base pairs in the target DNA. For example, a 3 finger domain recognized a sequence of 9 contiguous nucleotides, with a dimerization requirement of the nuclease, two sets of zinc finger triplets are used to bind an 18 nucleotide recognition sequence.

The type II CRISPR/Cas system from bacteria employs a crRNA and tracrRNA to guide the Cas endonuclease to its DNA target. The crRNA (CRISPR RNA) contains the region complementary to one strand of the double strand DNA target and base pairs with the tracrRNA (trans-activating CRISPR RNA) forming a RNA duplex that directs the Cas endonuclease to cleave the DNA target. As used herein, the term "guide nucleotide" relates to a synthetic fusion of two RNA molecules, a crRNA (CRISPR RNA) comprising a variable targeting domain, and a tracrRNA. In an aspect, the guide nucleotide comprises a variable targeting domain of 12 to 30 nucleotide sequences and a RNA fragment that can interact with a Cas endonuclease.

In an aspect, the guide nucleotide can be introduced indirectly by introducing a recombinant DNA molecule comprising the corresponding guide DNA sequence operably linked to a plant specific promoter that is capable of transcribing the guide nucleotide in the plant cell. The term "corresponding guide DNA" includes a DNA molecule that is identical to the RNA molecule but has a "T" substituted for each "U" of the RNA molecule. In an aspect, the guide nucleotide is introduced via particle bombardment or using the disclosed methods and compositions for *Agrobacterium* transformation of a recombinant DNA construct comprising the corresponding guide DNA operably linked to a plant U6 polymerase III promoter.

In an aspect, the RNA that guides the RNA Cas9 endonuclease complex, is a duplexed RNA comprising a duplex crRNA-tracrRNA. One advantage of using a guide nucleotide versus a duplexed crRNA-tracrRNA is that only one expression cassette needs to be made to express the fused guide nucleotide.

The terms "target site," "target sequence," "target DNA," "target locus," "genomic target site," "genomic target sequence," and "genomic target locus" are used interchangeably herein and refer to a polynucleotide sequence in the genome (including choloroplastic and mitochondrial DNA) of a plant cell at which a double-strand break is induced in the plant cell genome by a Cas endonuclease. The target site can be an endogenous site in the plant genome, or alternatively, the target site can be heterologous to the plant and thereby not be naturally occurring in the genome, or the target site can be found in a heterologous genomic location compared to where it occurs in nature.

Unless defined otherwise, all technical and scientific terms used herein have the same meaning as commonly understood by one of ordinary skill in the art to which the invention pertains. The following definitions supplement those in the art and are directed to the current application and are not to be imputed to any related or unrelated case, e.g., to any commonly owned patent or application. Although any methods and materials similar or equivalent to those described herein can be used in the practice for testing of the present invention, the preferred materials and methods are described herein. Accordingly, the terminology used herein is for the purpose of describing particular embodiments only, and is not intended to be limiting.

As used in this specification and the appended claims, the singular forms "a," "an" and "the" include plural referents unless the context clearly dictates otherwise. Thus, for example, reference to "a protein" includes two or more proteins; reference to "a cell" includes mixtures of cells, and the like.

The term "agronomic phenotype" or "agronomic characteristics" refers to different measurements collected during the growing season to determine fitness of the plant, line, hybrid, inbred, or variety. Examples of agronomic phenotypes collected include seedling emergence, seedling vigor, seedling chlorosis, ear height, plant height, lodging, maturity, and yield.

"Acceptable agronomic phenotype" or "acceptable level" refers to the level of fitness of a plant, line, inbred, hybrid, or variety as compared to known commercial standards for a specific trait of interest. "Setting the level of criteria" refers to obtaining a consensus from experts in the field of interest to determine the acceptable agronomic phenotype for specific traits of interest that are needed for successful plant production.

An "allele" or "allelic variant" is any of one or more alternative forms of a gene or genetic marker. In a diploid cell or organism, the two alleles of a given gene (or marker) typically occupy corresponding loci on a pair of homologous chromosomes.

The term "association" or "associated with" in the context of this invention refers to one or more genetic marker alleles and phenotypic trait alleles that are in linkage disequilibrium, i.e., the marker genotypes and trait phenotypes are found together in the progeny of a plant or plants more often than if the marker genotypes and trait phenotypes segregated independently.

Backcrossing refers to a process in which a breeder crosses a hybrid progeny variety back to one of the parental genotypes one or more times. Backcross generations are denoted by "BCn", where n is the number of backcrosses to the same recurrent parent. Different filial generations can be created from backcrossing for testing, described as "BCnFx", where n is the number of backcrosses and x is the number of the filial generation created by selfing after backcrossing.

"Backcross progeny" refers to progeny plants produced by crossing a plant with plants of another line that comprise a desired trait or locus, selecting F1 progeny plants that comprise the desired trait or locus, and crossing the selected F1 progeny plants with the plants one or more times to produce backcross progeny plants that comprise said trait or locus. A backcross population is a set of backcross progeny from the F1 plants.

A "bi-parental population" is any derived population of individuals (F2, F3, RIL, et that are started by crossing 2 parental lines.

A "breeding cycle" describes the separation between two inbred parents and an inbred offspring of these parents. A breeding cycle can include, for example, crossing two inbred lines to produce an F1 hybrid, selfing the F1 hybrid, and selfing several more times to produce the inbred offspring. A breeding cycle optionally includes one or more backcrosses to one of the inbred parents. The separation between an inbred and a single cross F1 hybrid or between two single cross F1 hybrids can also be described in terms of breeding cycles. To determine the breeding cycle distance of a single cross F1 hybrid to an inbred, the breeding cycle difference between the inbred and each inbred parent of the hybrid is determined; the larger of these two numbers is the number of breeding cycles separating the F1 single cross hybrid and the inbred. To determine the breeding cycle distance of a first single cross F1 hybrid to a second single cross F1 hybrid, all possible combinations of the first hybrid's inbred parents with the second hybrid's inbred parents are compared to each other, and the breeding cycle distance between the two hybrids equals the largest distance between any one of these combinations of inbred parents.

The term "bulking" refers to combining together plants to create a larger population, or combining together plants that are deemed to be similar, such as having the same zygosity. A "bulk population" refers to a group of plants that are combined together to represent the specific pedigree. A "bulked pool of plants" are defined by having the same pedigree and the same zygosity of the gene(s) of interest, usually a homozygous positive pool of plants that is compared to a homozygous negative pool of plants from the same pedigree.

"Crossing" is the action by which two parental lines are sexually mated, producing an F1 progeny.

A "diploid plant" is a plant that has two sets of chromosomes, typically one from each of its two parents.

A "diverse panel of plant lines" is defined as a set of germplasm that is genetically or phenotypically diverse, and have been selected to represent the genetic or phenotypic diversity of germplasm relevant for breeding activities more generally.

A "doubled haploid" or "doubled haploid plant or cell" is one that is developed by the doubling of a haploid set of chromosomes. A plant or seed that is obtained from a doubled haploid plant that is selfed any number of generations may still be identified as a doubled haploid plant. A doubled haploid plant is considered a homozygous plant. A plant is considered to be doubled haploid if it is fertile, even if the entire vegetative part of the plant does not consist of the cells with the doubled set of chromosomes. For example, a plant will be considered a doubled haploid plant if it contains viable gametes, even if it is chimeric.

A "double haploid plant population" is a set of double haploid lines derived from the same cross, having a common ancestor at the initiation of the double haploid production process.

An "established breeding population" is a collection of plants produced by and/or used as parents in a breeding program, e.g., a commercial breeding program. The members of the established breeding population have typically been well-characterized; for example, several phenotypic traits of interest may have been evaluated, e.g., under different environmental conditions, at multiple locations, and/or at different times.

"$F_1$" refers to the first filial generation, the progeny of a mating between two individuals or between two inbred lines. "Advanced generations" or "advanced filial generations" are the $F_2$, $F_3$, and later generations produced from the $F_1$ progeny by self-pollination "selfing" or sexual crosses (e.g., with other $F_1$ progeny, with an inbred line, etc.).

An "F2 derived population of segregating individuals" refers to the filial generation of individuals produced by self-pollinating an F1 cross. Individual plants within an F2 population with typical Mendelian inheritance would 25% of the time be homozygous positive, 50% of the time be hemizygous, and 25% of the time be homozygous negative, which is why these populations are referred to as having segregating individuals.

The term F2:3 (bulk) generally refers to F2-derived F3 plants, where the F3 plants are bulked (as derived from each F2) keeping their parentage intact. For example, the F2 plants that are hemizygous are discarded and the F2 plants that are homozygous positive or negative are selfed to create F3 bulked plants. In this example, the F2 plants are derived from selfing F1 plants and the F2 plants are not bulked but are retained separately to maintain the parental relationship to create the F3 bulked plants. In an aspect, F3 bulk derived from the F2 plants is a balanced bulk, where each F2 plant contributes equally to the bulk. For example, if there are 10 F2 homozygous positive (++) plants, and if 100 seeds of the bulk are needed, each F2 plant would contribute 10 seeds to the bulk. In this aspect, each F2 plant is represented equivalently (genetically) in the bulk, which minimized imbalance caused by allele frequency. By keeping the plants separated at the F2 stage, balanced bulk at F3 is achieved.

The term "gene" is used broadly to refer to any nucleic acid associated with a biological function. Genes typically include coding sequences and/or regulatory sequences required for expression of such coding sequences.

A "genetic marker" is a nucleotide or a polynucleotide sequence that is present in a plant genome and that is polymorphic in a population of interest, or the locus occupied by the polymorphism, depending on context. Genetic markers include, for example, SNPs, indels, SSRs, RFLPs, RAPDs, and AFLPs, among many other examples. Genetic markers can, e.g., be used to locate on a chromosome genetic loci containing alleles which contribute to variability in expression of phenotypic traits. Genetic markers also refer to polynucleotide sequences complementary to the genomic sequences, such as sequences of nucleic acids used as probes.

A "genome edit" or "genomic modification" is any genetic diversity that arises from targeted mutagenesis using biotechnology tools such as CRISPR, TALENs, etc.

"Genotype" refers to the genetic constitution of a cell or organism. An individual's "genotype for a set of genetic markers" consists of the specific alleles, for one or more genetic marker loci, present in the individual. Genotype is represented by "G."

"Germplasm" is the totality of the genotypes of a population or other group of individuals (e.g., a species). Germplasm can also refer to plant material, e.g., a group of plants that act as a repository for various alleles. "Adapted germplasm" refers to plant materials of proven genetic superiority, e.g., for a given environment or geographical area, while "non-adapted germplasm," "raw germplasm," or "exotic germplasm" refers to plant materials of unknown or unproven genetic value, e.g., for a given environment or geographical area; as such, non-adapted germplasm refers to plant materials that are not part of an established breeding population and that do not have a known relationship to a member of the established breeding population. Germplasm is represented by "G" and may be interchangeable with "genotype."

A "haplotype" is the set of alleles an individual inherited from one parent. A diploid individual thus has two haplotypes. The term haplotype is often used in a more limited sense to refer to physically linked and/or unlinked genetic markers (e.g., sequence polymorphisms) associated with a phenotypic trait. A "haplotype block" (sometimes also referred to in the literature simply as a haplotype) is a group of two or more genetic markers that are physically linked on a single chromosome (or a portion thereof). Typically, each block has a few common haplotypes, and a subset of the genetic markers (i.e., a "haplotype tag") can be chosen that uniquely identifies each of these haplotypes.

Material that is "homozygous positive" are progeny from a cycle of self-pollinating and have 2 copies of an allele of interest. Similarly, material that is "homozygous negative" are progeny from a cycle of self-pollinating and segregate null for both copies of an allele of interest.

A "hybrid," "hybrid plant," or "hybrid progeny" is an individual produced from genetically different parents (e.g., a genetically heterozygous or mostly heterozygous individual). Typically, the parents of a hybrid differ in several important respects. Hybrids are often more vigorous than either parent, but they cannot breed true.

An "inbred line" of plants is a genetically homozygous or nearly homozygous population. An inbred line, for example, can be derived through several cycles of selfing. Inbred lines breed true, e.g., for one or more phenotypic traits of interest. An "inbred," "inbred plant," or "inbred progeny" is a plant sampled from an inbred line.

The term "isoline" refers to near-isogenic lines, which are one or more breeding lines that are identical to each other in genetic makeup except for a gene or gene(s) of interest. Isolines can be created be selfing a single plant segregating for a gene of interest. In the next generation, the gene of interest will segregate 1:2:1 (1 homozygous positive: 2 heterozygous: 1 homozygous null). Individual plants that are homozygous positive or homozygous null for the gene of interest are selected, these plants are isolines to each other. The null is referred to as an "isogenic transgene null"

A "locus" is a position on a chromosome (e.g., of a gene, a genetic marker, or the like).

"MAS" or "marker assisted selection": Selection of plants based on a molecular assay of the gene(s) conferring a given trait/phenotype. A desirable feature of MAS is the ability to directly determine genotype without the need to expose plants to the precise environmental conditions required to observe the desirable trait in a whole-plant assay. Possible undesirable features of MAS include the infrastructure and cost versus other assays and/or the a priori need to know the causal genes or genetic markers linked to the desired trait gene(s).

An "assay", as used herein, is a method to determine the presence or absence of a transgene or gene of interest. For example, a "molecular assay" is a diagnosis assay using molecular biology techniques to determine presence or absence of a transgene or gene of interest. This assay can be in the form of using PCR to amplify the transgene or gene of interest, or other techniques involving use of molecular markers linked to the transgene or gene of interest. The molecular assay may also be utilized to determine zygosity.

The term "nucleic acid" encompasses any physical string of monomer units that can be corresponded to a string of nucleotides, including a polymer of nucleotides (e.g., a typical DNA or RNA polymer), PNAs, modified oligonucleotides (e.g., oligonucleotides comprising bases that are not typical to biological RNA or DNA, such as 2'-O-methylated oligonucleotides), and the like. A nucleic acid can be e.g., single-stranded or double-stranded. Unless otherwise indicated, a particular nucleic acid sequence of this invention optionally comprises or encodes complementary sequences, in addition to any sequence explicitly indicated.

A "pedigree" is a record of the ancestor lines, individuals, or germplasm for an individual or a family of related individuals.

The phrase "phenotypic trait" refers to the appearance or other detectable characteristic of a plant, resulting from the interaction of its genome with the environment. "Phenotyping" is the action of collecting phenotypic trait data.

The term "plant" includes reference to whole plants, plant organs (e.g., leaves, stems, roots, etc.), seeds and plant cells and progeny of same. "Plant cell", as used herein includes, without limitation, seeds, suspension cultures, embryos, meristematic regions, callus tissue, leaves, roots, shoots, gametophytes, sporophytes, pollen, and microspores.

A "population" or "plant population" is a collection of plants. The collection includes at least two plants, and can include, for example, 10 or more, 50 or more, 100 or more, 500 or more, 1000 or more, or even 5000 or more plants. The members of the population can be related and/or unrelated to each other; for example, the plants can have known pedigree relationships to each other.

The term "plurality" refers to more than half of the whole. For example, a plurality of a population is more than half the members of that population.

A "polynucleotide sequence" or "nucleotide sequence" is a polymer of nucleotides (an oligonucleotide, a DNA, a nucleic acid, etc.) or a character string representing a nucleotide polymer, depending on context. From any specified polynucleotide sequence, either the given nucleic acid or the complementary polynucleotide sequence (e.g., the complementary nucleic acid) can be determined.

The term "PCR" refers to polymerase chain reaction, a molecular biology technique used to amplify a segment of DNA that is of interest.

The term "progeny" refers to the descendant(s) of a particular plant (self-pollinated) or pair of plants (cross-pollinated). The descendant(s) can be, for example, of the $F_1$, the $F_2$, or any subsequent generation. As used herein, the term "progeny" refers to any plant that results from a natural or assisted breeding of one or more plants. For example, progeny plants can be generated by crossing two plants (including, but not limited to crossing two unrelated plants, backcrossing a plant to a parental plant, intercrossing two plants, etc.), but can also be generated by selfing a plant, creating an inbred (e.g., a double haploid), or other techniques that would be known to one of ordinary skill in the art. As such, a "progeny plant" can be any plant resulting as progeny from a vegetative or sexual reproduction from one or more parent plants or descendants thereof. For instance, a progeny plant can be obtained by cloning or selfing of a parent plant or by crossing two parental plants and include selfings as well as the $F_1$ or $F_2$ or still further generations. An $F_1$ is a first-generation progeny produced from parents at least one of which is used for the first time as donor of a trait, while progeny of second generation ($F_2$) or subsequent generations ($F_3$, $F_4$, and the like) are in some embodiments specimens produced from selfings (including, but not limited to double haploidization), intercrosses, backcrosses, or other crosses of $F_1$ individuals, $F_2$ individuals, and the like. An $F_1$ can thus be (and in some embodiments, is) a hybrid resulting from a cross between two true breeding parents (i.e., parents that are true-breeding are each homozygous for a trait of interest or an allele thereof, and in some embodiments, are inbred), while an $F_2$ can be (and in some embodiments, is) a progeny resulting from self-pollination of the $F_1$ hybrids.

A "qualitative trait" is a phenotypic trait that is controlled by one or a few genes that exhibit major phenotypic effects. Because of this, qualitative traits are typically simply inherited. Examples include, but are not limited to, flower color, cob color, and disease resistance such as Northern corn leaf blight resistance.

A "quantitative trait" is a phenotypic trait that can be described numerically (i.e., quantitated or quantified). A quantitative trait typically exhibits continuous variation between individuals of a population; that is, differences in the numerical value of the phenotypic trait are slight and grade into each other. Frequently, the frequency distribution in a plant population of a quantitative phenotypic trait exhibits a bell-shaped curve. A quantitative trait is typically the result of a genetic locus interacting with the environment or of multiple genetic loci (QTL) interacting with each other and/or with the environment. Examples of quantitative traits include plant height and yield.

The term "quantitative trait locus" ("QTL") or the term "marker trait association" refers to an association between a genetic marker and a chromosomal region and/or gene that affects the phenotype of a trait of interest. Typically, this is determined statistically, e.g., based on one or more methods published in the literature. A QTL can be a chromosomal region and/or a genetic locus with at least two alleles that differentially affect the expression of a phenotypic trait (either a quantitative trait or a qualitative trait).

The term "relative maturity" refers to the point in time after physiological maturity when a hybrid or variety can be harvested with minimal final yield loss or damage to final seed quality. For soybean relative maturity zones have been developed across North America to describe adaptability of soybean varieties. RM zones range from RM00 (Northern Minnesota, Northern North Dakota) to RM8 (Southern Georgia, Florida) The phrase "recombinant inbred line" or "RIL" refers to a line that has a permanent set of recombination event(s) between chromosomes that are inherited from two or more inbred parental lines. These recombination events become fixed by self-pollinating the line for several generations. A population of different recombinant inbred lines from the same cross or set of crosses can be used to map locations of DNA markers or QTL.

The phrase "sexually crossed" or "sexual reproduction" in the context of this invention refers to the fusion of gametes to produce seed by pollination. A "sexual cross" or "cross-pollination" is pollination of one plant by another. "Selfing" is the production of seed by self-pollinization, i.e., pollen and ovule are from the same plant. The term "similar environmental conditions" refers to physical locations where plants are grown and evaluated for their trait effects, and may refer to a single field, a greenhouse, a shade house, or different fields, greenhouses, or shade houses or other types of growing locations where climatic conditions are comparable.

A "single cross $F_1$ hybrid" is an $F_1$ hybrid produced from a cross between two inbred lines.

A "tester" is a line or individual plant with a standard genotype, known characteristics, and established performance. A "tester parent" is a plant from a tester line that is used as a parent in a sexual cross. Typically, the tester parent is unrelated to and genetically different from the plant(s) to which it is crossed. A tester is typically used to generate $F_1$ progeny when crossed to individuals or inbred lines for phenotypic evaluation.

The term "trait performance" or "trait effect" is represented by "T", and refers to the average phenotypic contrast between a germplasm that contains the trait as compared to a germplasm that lacks the trait.

The term "trait by genotype interactions" is represented by "trait by genotype interaction," "trait by genotype, or "TxG."

The term "trait by genotype by environment interactions" is represented by "trait by genotype by environment interaction," "trait by genotype by environment", or "TxGxE."

A "transgene breeding value" is the calculated average difference of a measured phenotype when adding a transgene to a set of germplasm as compared to the same set of germplasm without the presence of the transgene.

A "transgenic plant" is a plant into which one or more exogenous polynucleotides have been introduced by any means other than sexual cross or selfing. Examples of means by which this can be accomplished are described below, and include *Agrobacterium*-mediated transformation, biolistic methods, electroporation, in planta techniques, and the like. Transgenic plants may also arise from sexual cross or by selfing of transgenic plants into which exogenous polynucleotides have been introduced.

A "variety" is a subdivision of a species for taxonomic classification. "Variety" is used interchangeably with the term "cultivar" to denote a group of individuals that are genetically distinct from other groups of individuals in a species. An agricultural variety is a group of similar plants that can be identified from other varieties within the same species by structural features and/or performance.

A "win/loss ratio" is the proportion of times a trait achieves the acceptable level set in the criterion compared with the proportion of time a trait fails to achieve that same criterion.

The term "whole genome molecular markers" refers to any given set of molecular markers that are assayed across the genome of a set of germplasm to define the genetic composition of a line. The whole genome molecular markers can be used define the genetic relationship of different germplasm to each other, and also used to define the "whole genome marker by transgene interaction" which is the calculated average difference of a measured phenotype when adding a transgene to a specific set of molecular markers that represent a germplasm as compared to the same set of molecular markers that represent a germplasm without the presence of that transgene.

The term "zygosity" refers to the similarity of alleles for a trait. For diploid species, homozygous positive refers to the organism possessing two copies of the same allele at the same locus, and heterozygous refers to the organism possessing one copy of one allele, and one copy of a different allele at the same locus.

A variety of additional terms are defined or otherwise characterized herein.

EXPERIMENTAL

Example 1. Utilizing Isolines and BC1F2:3 Bulks to Evaluate Transgenic Trait (T) and Transgenic Trait x Genotype (TxG) Agronomic Effects in Soybean Utilizing Isolines to Evaluate Transgenic Trait (T) Agronomic Effects A transgenic construct with one gene of interest providing a strong level of efficacy was evaluated in isoline field trials to identify potential agronomic effects. Isolines were developed as described in FIG. 1. Nine events were selected based upon T0 and T1 trait efficacy in greenhouse studies and Mendelian segregation in the T1 and T2 generation. T3 isolines were created for each event for agronomic testing in multiple location field trials. In Year1, homozygous positive and homozygous negative isolines for each of the nine events were grown in an isoline agronomic yield test, consisting of a randomized complete block design, blocked by construct with paired rows 4.57 m in length with 0.76 m row spacing. Homozygous positive and homozygous negative isolines for each specific event were grown in a front-to-back arrangement to minimize environmental variance.

In Year1, the isoline agronomic yield tests were grown in two replications near Grinnell, IA, Griswald, IA, Johnston, IA, Stuart, IA, Winterset, IA, Washington, IA, Marshall, MO, Lawrence, KS, Wichita, KS), Pesotum, IL, Morrisonville, IL, and Crawfordsville, IN In Year2, the isoline experiments were a randomized complete block design, blocked by construct with paired rows 4.57 m in length with 0.76 m row spacing. The Year2 trials were grown in two replications near Johnston, IA, Stuart, IA, Winterset, IA, Washington, IA, Marshall, MO, Lawrence, KS, Seneca, KS, Wichita, KS, Pesotum, IL, Milmine IL, Morrisonville, IL, Crawfordsville, IN, and Farmersburg, IN In both Year1 and Year2, growth of the isolines throughout the season was measured at the V4, R2, and R8 growth stages by selecting an average plant for each plot and measuring the distance from the ground to the top leaf (inches). Maturity (days after planting when 95% of pods had the final mature color) and yield data (bu/ac) were collected. For all data collected, best linear unbiased predictions (BLUPs) were developed for each positive and negative isoline.

In comparing the V4, R2, and R8 height data across both Year1 and Year2, events 1, 2, 5, 7, 8, and 9 had significantly shorter positive isolines compared to the negative isoline of the same event (Table 1). Events 3 and 4 had positive isolines significantly shorter at V4, R2, and R8 in Year1 (Table 1). In Year2, event 3 was not significant (NS) at V4 and R8, while event 4 was NS at V4 and R2 (Table 1). Event 6 was NS at V4 in Year1, but for all other measurements the event 6 positive isoline was significantly shorter compared to the negative isoline in Year1 and Year2 (Table 1).

For maturity in Year1 and Year2, events 1, 2, 3, 6, and 8 had positive isolines that were significantly earlier in maturity compared to negative isolines from the same event, while event 5 was NS (Table 1). Events 4, 7, and 9 were NS in Year1, but in Year2 the positive isolines were significantly earlier in maturity compared to negative isolines from the same event (Table 1).

Due to the significant maturity effects observed for most of the events, yield BLUP data were adjusted by using the maturity as a covariate in the analysis. In both Year1 and Year2, events 1, 2, 5, 6, 7, 8, and 9 had positive isolines that were significantly lower in yield compared to negative isolines from the same event (Table 1). In Year1, the positive isoline from event 3 was significantly lower in yield compared to the negative isoline, but was NS in Year2 (Table 1). Conversely, event 4 was NS for yield in Year1 and the positive isoline significantly lower in yield (0.05 level) in Year2 (Table 1). These data demonstrate how isolines can be utilized to evaluate different transgenic events from the same construct for potential agronomic effects.

TABLE 1

Year1 and Year2 Agronomic differences of BLUPs (pos-neg) for isolines for nine transgenic events from one construct

| Event | Year | V4 Height[1] Diff1 | | R2 Height[1] Diff1 | | R8 Height[1] Diff1 | | Maturity[2] Diff2 | | Yield3 Diff3 | |
|---|---|---|---|---|---|---|---|---|---|---|---|
| Event 1 | Year1 | −2.33 | *** | −6.28 | *** | −9.44 | *** | −8.50 | *** | −23.75 | *** |
| Event 1 | Year2 | −2.70 | *** | −6.68 | *** | −9.71 | *** | −12.00 | *** | −28.55 | *** |
| Event 2 | Year1 | −1.56 | *** | −3.78 | *** | −8.56 | *** | −6.00 | *** | −10.92 | *** |
| Event 2 | Year2 | −2.72 | *** | −4.08 | *** | −6.02 | *** | −12.00 | *** | −16.32 | *** |
| Event 3 | Year1 | −1.83 | *** | −4.06 | *** | −9.13 | *** | −11.00 | *** | −9.98 | *** |

TABLE 1-continued

Year1 and Year2 Agronomic differences of BLUPs (pos-neg) for isolines for nine transgenic events from one construct

| Event | Year | V4 Height[1] Diff1 | | R2 Height[1] Diff1 | | R8 Height[1] Diff1 | | Maturity[2] Diff2 | | Yield3 Diff3 | |
|---|---|---|---|---|---|---|---|---|---|---|---|
| Event 3 | Year2 | −0.15 | | −1.74 | * | −0.64 | | −4.00 | *** | 0.35 | |
| Event 4 | Year1 | −1.27 | ** | −2.34 | ** | −7.31 | *** | −0.50 | | −0.19 | |
| Event 4 | Year2 | −0.25 | | −0.58 | | −4.79 | *** | −6.00 | *** | −3.96 | * |
| Event 5 | Year1 | −2.75 | *** | −5.50 | *** | −8.75 | *** | −0.50 | | −21.04 | *** |
| Event 5 | Year2 | −2.38 | *** | 4.53 | *** | −6.32 | *** | | | −25.81 | *** |
| Event 6 | Year1 | −0.89 | | −4.33 | *** | −8.31 | *** | −3.50 | *** | −16.03 | *** |
| Event 6 | Year2 | −1.60 | *** | 4.45 | *** | −7.57 | *** | −9.00 | *** | −17.47 | *** |
| Event 7 | Year1 | −1.96 | *** | −6.28 | *** | −10.19 | *** | −1.00 | | −15.19 | *** |
| Event 7 | Year2 | −3.00 | *** | −6.63 | *** | −9.14 | *** | −11.00 | *** | −20.91 | *** |
| Event 8 | Year1 | −2.56 | *** | −7.22 | *** | −10.31 | *** | −3.00 | *** | −26.21 | *** |
| Event 8 | Year2 | −2.00 | *** | −6.16 | *** | −8.64 | *** | −12.00 | *** | −28.28 | *** |
| Event 9 | Year1 | −4.06 | *** | −10.56 | *** | −15.19 | *** | −0.50 | | −34.67 | *** |
| Event 9 | Year2 | −4.65 | *** | −8.53 | *** | −13.07 | *** | −11.00 | *** | −36.41 | *** |

[1]Height (inches from ground to top of plant) difference (positive - negative)
[2]Maturity (days from planting until 95% of pods within a plot are final mature color) difference (positive - negative)
3Yield (bu/ac) difference (positive - negative) adjusted for maturity
*, , * significant at the 0.05, 0.01 and 0.001 level, respectively Utilizing $BC1F_2$ Derived Bulks to Evaluate Transgenic Trait x Genotype (TxG) Agronomic Effects To determine if breeding would address some of the agronomic issues discovered in the isoline trials, six of the events were selected for backcrossing. Event 4 was selected based upon the lowest agronomic effects, events 3, 6 and 7 were selected for medium agronomic effects, and events 8 and 9 were selected based upon the highest agronomic effects. Homozygous positive T4 plants of each event were crossed to up to seven elite soybean varieties with different relative maturities (RM) (RM25, RM31, RM32, RM34, RM38-1, RM38-2, and RM39). The elite varieties were selected based upon pedigree diversity and level of polymorphism when compared to the transformed variety. Initial cross F1s were then backcrossed to the same elite parent and populations were developed as described in FIG. 2. The BC1F1 plants were allowed to self and generate a random population of BC1F2 plants. Tissue samples from approximately 100 BC1F2 plants per BC1 population were analyzed by PCR assay to identify transgene zygosity. Approximately 25 homozygous positive BC1F2 plants for each population were bulked together after harvest to create a transgene positive BC1F2:3 bulk seed lot. Similarly, approximately 25 homozygous negative BC1F2 plants for each population were bulked together after harvest to create a negative BC1F2:3 bulk seed lot. BC1F2 plants that were heterozygous for the transgene were discarded in each population.

BC1F2:3 bulk yield test experiments were a randomized complete block design, blocked by construct with paired rows 4.57 m in length with 0.76 m row spacing. The Year3 bulk yield tests were grown as two replications at Johnston, IA and Griswald, IA. Maturity (days after planting when 95% of pods had the final mature color) and yield data (bu/ac) were collected. In the statistical analysis, yield data were adjusted for maturity to enable direct comparison of transgene positive to transgene negative BC1F2:3 bulks within the same population.

Seed from Year3 yield test were grown in multiple location yield trials in Year4 as BC1F2:4 yield tests. The Year4 yield tests were a randomized complete block design, blocked by background with paired rows 4.57 m in length with 0.76 m row spacing. Homozygous positive or homozygous null BC1F2:4 bulks were grown in 2 replications at Griswald, IA, Johnston, IA, Montezuma, Stuart, IA, Washington, IA, and Winterset IA. Maturity (days after planting when 95% of pods had the final mature color) and yield data (bu/ac) were collected. For all agronomic data collected, best linear unbiased predictions (BLUPs) were developed for each positive and negative bulk.

There were some potential TxG interactions observed across the different events tested as BC1F2 derived bulks. In the RM25 and RM38-1 backgrounds, all events had BC1F2 derived positive bulks that were significantly lower in yield compared to negative bulks in both Year3 and Year4 (Table 2). In RM34 and RM38-2 backgrounds, Event 4 was NS for yield in Year3 and had a significant difference at the 0.05 level in Year4 (Table 2). All the other events had positive BC1F2 derived bulks with significantly lower yield compared to their respective null bulk in the RM34 and RM38-2 backgrounds (Table 2). Event 4 was NS for yield in both Year3 and Year4 in the RM31 and RM39 backgrounds, while Event 6 was NS for yield in RM31 and significantly different for yield in RM39 (Table 2).

Across all backgrounds, all events had positive F2 derived bulks that were significantly lower in yield compared to negative F2 derived bulks in Year3, Year4 and combined Year3+Year4 data (Table 2). A similar trend was observed between the isoline trials and the BC1F2 bulk derived trials, wherein Event 4 had the smallest overall yield difference (Table 2). Events 3, 4, and 7 (classified as having the medium yield impact as isolines) tended to have medium yield impact in the BC1F2 derived bulk trials and Events 8 and 9 (highest yield effect as isolines) tended to have the largest yield impact in the BC1F2 derived bulk yield tests (Table 2). These data support that breeding to the BC1 generation did not help to correct detrimental yield effects observed in the isoline trials for the events tested. However, utilizing the F2 derived bulk method for yield testing allowed for yield testing these events 3 years earlier compared to the estimated timeline for full BC5 backcross conversion and line development.

TABLE 2

BLUP Yield differences (pos (positive)-neg (negative), adjusted for maturity) for
BC1F2:3 bulks (Year3) and BC1F2:4 bulks (Year4) of selected events backcrossed into
different genetic backgrounds
BLUP Yield Difference Positive bulk - Negative Bulk (bu/ac)

| Event | Effect1 | Year3 | | Year4 | | Year3 + Year4 | | Year3 | | Year4 | | Year3 + Year4 | |
|---|---|---|---|---|---|---|---|---|---|---|---|---|---|
| | | RM25 | | | | | | RM38-1 | | | | | |
| Event3 | Med | -20.8 | *** | -15.9 | *** | -18.3 | *** | -11.5 | * | -18.4 | *** | -15.0 | *** |
| Event4 | Low | -24.1 | *** | -6.1 | * | -15.1 | *** | -12.2 | * | -5.6 | * | -8.9 | * |
| Event6 | Med | -36.2 | *** | -5.6 | * | -20.9 | *** | -27.5 | *** | -9.9 | *** | -18.7 | *** |
| Event7 | Med | -34.6 | *** | -21.5 | *** | -28.1 | *** | -25.0 | *** | -19.7 | *** | -22.4 | *** |
| Event8 | High | -16.4 | *** | -4.9 | * | -10.7 | *** | -24.6 | *** | -24 | *** | -24.3 | *** |
| Event9 | High | -42 | *** | -5.7 | ** | -23.8 | *** | -37.4 | *** | -9.2 | *** | -23.3 | *** |
| | | RM32 | | | | | | RM34 | | | | | |
| Event3 | Med | -26.5 | *** | -15.2 | *** | -20.9 | *** | -26.1 | *** | -11.6 | *** | -18.9 | *** |
| Event4 | Low | -11.1 | | -4.1 | | -7.6 | * | -7.3 | | -6.3 | * | -6.8 | * |
| Event6 | Med | | | | | | | -12.0 | ** | -6.3 | ** | -9.2 | ** |
| Event7 | Med | | | | | | | -34.6 | *** | -28.7 | *** | -31.7 | *** |
| Event8 | High | -32.5 | *** | -19 | *** | -25.7 | *** | -20.6 | *** | -18.4 | *** | -19.5 | *** |
| Event9 | High | -25.3 | *** | -6.9 | ** | -16.1 | *** | -46.9 | *** | -31.4 | *** | -39.1 | *** |
| | | RM38-2 | | | | | | RM31 | | | | | |
| Event3 | Med | -11.4 | * | -6.4 | * | -8.9 | *** | -25.8 | *** | -15.2 | *** | -20.5 | *** |
| Event4 | Low | -4.6 | | -5.7 | * | -5.1 | * | 0.8 | | 1.7 | | 1.3 | |
| Event6 | Med | -14.6 | *** | -18.8 | *** | -16.7 | *** | -5.1 | | -4.8 | | -5.0 | |
| Event7 | Med | -16.3 | *** | -14.5 | *** | -15.4 | *** | | | | | | |
| Event8 | High | -12.0 | *** | -5.3 | * | -8.6 | *** | -32.8 | *** | -7 | ** | -19.9 | *** |
| Event9 | High | | | | | | | | | | | | |
| | | RM39 | | | | | | ALL Backgrounds | | | | | |
| Event3 | Med | -18.5 | *** | -12.5 | *** | -15.5 | *** | -20.1 | *** | -13.6 | *** | -16.9 | *** |
| Event4 | Low | -6.4 | | -0.5 | | -3.5 | | -9.3 | *** | -3.8 | *** | -6.6 | *** |
| Event6 | Med | -28.9 | *** | -19.7 | *** | -24.3 | *** | -20.7 | *** | -10.8 | *** | -15.8 | *** |
| Event7 | Med | -18.7 | *** | -6.1 | ** | -12.4 | *** | -25.9 | *** | -18.1 | *** | -22.0 | *** |
| Event8 | High | | | | | | | -23.1 | *** | -13.1 | *** | -18.1 | *** |
| Event9 | High | | | | | | | -37.9 | *** | -15.8 | *** | -25.6 | *** |

1 Agronomic effect characterization from isoline agronomic trials
2 Yield (bu/ac) difference (positive bulk -negative bulk) adjusted for maturity
*, , * significant at the 0.05, 0.01 and 0.001 level, respectively

Example 2: Soybean Isoline and F2:3 Bulk Agronomic Testing

Transgenic Trait (T) Testing Using Isolines

Five constructs were created to generate a compositional shift of final protein and oil content in soybean seed. Construct 1 event 1 and construct 1 event 2 share the same promoter driving a gene of interest (GOI). The five constructs differ in the combination of promoter and GOI used. A total of 15 events across constructs were used in this study. Events for each construct were selected based upon T0 and T1 trait efficacy in greenhouse studies, simple insertion pattern as determined by southern analysis, and Mendelian segregation in the T1 and T2 generation. T3 isolines were created for each event for agronomic testing in multiple location field trials by selecting for trait zygosity in the T2 generation and selfing subsequent generations (FIG. 1).

In Year 2, homozygous positive and homozygous negative isolines for all 15 events were grown in a randomized complete block design, blocked by construct. Isolines for each specific event were grown in a front-to-back arrangement to minimize environmental variance. All isoline agronomic test plots were paired rows 4.57 m in length with 0.76 m row spacing. The isoline experiments were three replications grown near Johnston, IA, Stuart, IA, Washington, IA, Lawrence, KS, Seneca, KS, Wichita, KS, Crawfordsville, IN, Farmersburg, IN, Oxford, IN, Milmine, IL, Morrisonville, IL, and Marshall, MO Emergence of the plot was measured as a score from 1-9 where a score of 1 indicates poor emergence and 9 is emergence comparable to elite check varieties. Maturity (days after planting when 95% of pods had the final mature color) and yield data (kg/ha) were collected. For all data collected, best linear unbiased predictions (BLUPs) were developed for each positive and negative isoline.

Transgenic Trait x Genotype (TxG) Testing Using F2:3 Bulks

TxG testing material was developed utilizing the same 15 transgenic events in the isoline agronomic testing described above. T1 plants of each event were identified for zygosity and positive plants were crossed to three elite soybean varieties (RM38-1, RM34, and RM38-2). The elite varieties were selected based upon similar maturity, pedigree diversity, and level of polymorphism when compared to the transformed variety. The F1 plants were allowed to self and generate a random population of F2 plants. Tissue samples from approximately 500 F2 plants per population were analyzed by PCR assays to identify transgene zygosity. Homozygous positive F2:3 bulks for each event by elite combination were then developed by bulking the seed derived from approximately 125 F2 transgene positive plants. Homozygous negative F2:3 bulks were created from approximately 125 F2 transgene negative plants within each population. F2 plants that were heterozygous for the transgene were discarded.

In Year2, homozygous positive and homozygous negative F2:3 bulks for all 15 event x elite combinations were grown in a randomized complete block design yield test blocked by event and background. For each population, the positive bulk and negative bulk were randomized and grown in front-to-back arrangement to minimize environmental variance. All yield test plots were paired rows 4.57 m in length with 0.76 m row spacing. F2:3 bulk yield test experiments were three replications grown at each of 8 locations near Johnston, IA, Grinnell, IA, Washington, IA, Lawrence, KS, Farmersburg, IN, Oxford, IN, Milmine, IL, and Marshall, MO Emergence of the plot was measured as a score from 1-9 where a score of 1 indicates poor emergence and 9 is emergence comparable to elite check varieties. Maturity (days after planting when 95% of pods had the final mature color) and yield data (kg/ha) were collected. For all data collected, best linear unbiased predictions (BLUPs) were developed for each positive and negative F2:3 bulk.

Isoline and F2:3 Bulk Agronomic Data Analysis

In examining the emergence data, Construct1 Event 2, Construct 5 Event 1, and Construct 5 Event 6 had positive isolines that were significantly earlier compared to negative isolines within the same event (Table 3). In the F2:3 bulk data, all events were not significantly different for emergence (Table 3). For maturity, Construct 1 event 1 and Construct 4 Event 1 had positive isolines that were significantly delayed in maturity compared to their event null isoline. Across all the constructs tested, all positive isolines were significantly later in maturity compared to all negative isolines (Table 3). The positive F2:3 bulks of Events 1 and 2 of Construct 1 showed a significant delay in maturity of 1.1 and 1.4 days, respectively. For Construct 4, the positive F2:3 event 1, and Construct 5 event 2 had F2:3 positive bulks that were not significantly different compared to their F2:3 negative bulk. All other events tested had F2:3 positive bulks that were significantly lower in yield compared to their F2:3 negative bulk (Table 3). Across all F2:3 populations tested, all positive bulks were significantly lower in yield (−2.11 bu/ac average) compared to all negative F2:3 bulks (Table 3).

When contrasting the isoline data to the F2:3 bulk data, the emergence of all positive isolines were significantly lower than all negative isolines, while no significant difference was detected in the F2:3 bulks (Table 3). The variability of the isoline data was greater compared to the variability of the F2:3 bulk data for emergence. Maturity of all positive isolines was approximately 1 day later compared to all negative isolines, while all positive F2:3 bulks was less than 1 day later in maturity compared to all negative F2:3 bulks (Table 3). The variance in maturity was larger for the isolines compared to the F2:3 bulks. For yield, all positive isolines were significantly lower compared to all negative isolines, and all positive F2 bulks were significantly lower in yield compared to all negative F2 bulks (Table 3). However, there was greater variability in the isoline yield data when compared to the F2:3 bulk yield data (Table 3). These data demonstrate the utility in using isolines to identify potential transgene (T) effects and how utilizing F2:3 bulks will have lower variability to enable event advancement selection and initial understanding of potential transgene x genotype (TxG) effects.

TABLE 3

Agronomic trait differences (positive - negative) comparing isoline and F2:3 bulk testing using five different constructs field tested in Year2.

| | | Isoline | | | F2:3 bulk | | |
|---|---|---|---|---|---|---|---|
| Construct | Event | Emergence Diff[2] | Maturity[1] Diff[2] | Yield Diff[2] | Emergence Diff[3] | Maturity[1] Diff[3] | Yield Diff[3] |
| Construct 1 | Event 1 | −0.33 | 1.67* | −2.95*** | −0.05 | 1.09* | −0.51** |
| Construct 1 | Event 2 | 0.43* | 1.51 | −3.62*** | −0.02 | 1.37* | 0.20* |
| Construct 2 | Event 1 | −0.34 | −0.37 | −2.99*** | 0.00 | −0.19 | 0.19 |
| Construct 2 | Event 2 | −0.36 | −0.09 | −2.30** | 0.024 | −0.55 | 0.30* |
| Construct 4 | Event 1 | −0.19 | 3.28** | −7.11*** | 0.09 | 2.61*** | 4.65*** |
| Construct 5 | Event 1 | 0.42* | 0.25 | 4.19*** | 0.16 | 0.64 | −0.58** |
| Construct 5 | Event 2 | 0.05 | 0.09 | −2.36** | 0.25 | −0.14 | 0.83 |
| Construct 5 | Event 3 | 0.05 | 0.58 | −1.24 | 0.14 | 0.27 | −1.02*** |
| Construct 5 | Event 4 | −0.16 | 0.69 | −2.61** | 0.12 | 0.26 | −1.34*** |
| Construct 5 | Event 5 | −0.18 | 0.64 | −2.03* | 0.16 | 0.29 | −0.70** |
| Construct 5 | Event 6 | 0.53* | 1.46 | −5.9*** | 0.08 | 0.78 | −2.87*** |
| Construct 5 | Event 7 | −0.03 | 0.47 | −0.67 | 0.17 | 0.23 | −1.33*** |
| Construct 5 | Event 8 | −0.18 | 0.75 | −2.47** | 0.13 | 0.10 | −0.55** |
| Construct 5 | Event 9 | −0.16 | 0.53 | −2.1** | 0.18 | −0.60 | −0.60** |
| Construct 5 | Event 10 | −0.20 | 0.31 | −1.17 | 0.13 | 0.50 | 0.97*** |
| All constructs all events | | 0.35*** | 1.05* | −3.72*** | 0.08 | 0.69* | −2.11*** |

[1]Maturity = days from planting until 95% of pods within a plot are final mature color
[2]Isoline difference = (all positive isolines - all negative isolines)
[3]F2:3 bulk difference = (F2:3 positive bulk - F2:3 negative bulk)
*, , * significant at the 0.05, 0.01 and 0.001 level, respectively bulk from Event 1 had a significant delay of 2.6 days in maturity (Table 3). Combining all F2:3 bulk data, the positive F2:3 bulks had a significantly later maturity compared to all negative F2:3 bulks tested (Table 3). Yield of the positive isoline was significantly lower than the corresponding null isoline for 12 of the 15 events tested (Table 3). Across all constructs tested, all positive isolines were significantly lower in yield (−3.72 bu/ac average) compared to all null isolines (Table 3). In the F2:3 bulks, Construct 2

Sorting Transgenic Events Using F2:3 Bulk Agronomic Data Analysis

A factor relied upon for using F2:3 bulk testing method is that it permits a rapid introgression of the transgene into various genetic backgrounds, thus facilitating the early characterization of possible TxG effects. Agronomic results for the 15 events show some TxG interaction (Table 4). The data shows transgene breeding values (TBVs) for silking across each of the 127 testers. The effect of the transgene in a single tester x construct combination (GDUSLK/10) is shown. There is significant TxG for GDUSLK. Measuring the effect of this construct in any single hybrid combination would either over- or underestimate the true breeding value. Using the association mapping method best approximates the true average effect of the construct across germplasm. For emergence, there were 9 events in the RM38-1 background where the positive F2:3 bulk had a significantly higher emergence score compared to the corresponding negative F2:3 bulk (Table 4). The RM34 and RM38-2 backgrounds were NS for emergence for all the events tested (Table 4). For maturity, construct 4 event 1 had positive F2:3 bulks that were significantly later in maturity compared to their negative F2:3 bulks in both backgrounds tested (Table 4). For 7 events in the RM38-2 background, the positive F2:3 bulk was significantly later in maturity compared to the negative F2:3 bulk of the same population (Table 2). For yield, only construct 1 event 2 (RM38-1) and construct 2 event 2 (RM38-1) populations were not significant (Table 2). All other F2:3 populations tested had positive F2:3 bulks that were significantly lower in yield compared to their negative F2:3 bulk (Table 4).

In examining the data, events from Construct 1 and Construct 2 did not have significant effects detected for emergence, while Construct 5 had a significant TxG effect in the RM38-1 background (Table 4). Construct 4 events had the most effect on maturity, with positive lines that were significantly later than positive lines by approximately 2 days (Table 4). Construct 4 events had the highest yield impact, with positive lines 6.48 and 6.35 bu/ac lower in yield compared to negative lines within the same background (Table 4). Construct 1 and Construct 2 events in general had the smallest yield effect across the different genetic backgrounds when compared to Construct 4 and Construct 5 events (Table 4).

Across the agronomic traits measured, Construct 4 had the largest effect on maturity and yield (Table 4). Construct 5 events in general had larger yield differences when compared to Construct1 and Construct 2 events (Table 4). These data demonstrate that using F2:3 bulks in different genetic backgrounds allow an initial examination of potential TxG effects. Events with the smallest agronomic effects can be selected for advanced testing, while events with large agronomic effects can be discarded.

TABLE 4

| | | | Year 2 Agronomic trait differences (F2:3 positive lines – F2:3 negative lines) for 15 events crossed into different genetic backgrounds. | | |
| Construct | Event | Back-ground | Emergence Diff[2] | Maturity[1] Diff[2] | Yield Diff[2] |
| --- | --- | --- | --- | --- | --- |
| Construct 1 | Event 1 | RM34 | −0.06 | 0.58 | −1.85** |
| Construct 1 | Event 1 | RM38-2 | −0.01 | 0.76* | −1.71* |
| Construct 1 | Event 2 | RM38-1 | 0.11 | 0.62 | −1.25 |
| Construct 1 | Event 2 | RM38-2 | −0.01 | 0.78* | −1.78* |
| Construct 2 | Event 1 | RM34 | 0.04 | 0.17 | −1.66* |
| Construct 2 | Event 1 | RM38-2 | 0.09 | 0.36 | −1.52* |
| Construct 2 | Event 2 | RM38-1 | 0.2 | 0.17 | −1.44 |
| Construct 2 | Event 2 | RM38-2 | 0.09 | 0.33 | −1.97** |
| Construct 4 | Event 1 | RM34 | 0.13 | 1.86*** | −6.48*** |
| Construct 4 | Event 1 | RM38-2 | 0.18 | 2.04*** | −6.35*** |
| Construct 5 | Event 1 | RM38-1 | 0.24** | 0.32 | −1.59** |
| Construct 5 | Event 1 | RM34 | 0.07 | 0.29 | −2.25*** |
| Construct 5 | Event 1 | RM38-2 | 0.13 | 0.47* | −2.12*** |
| Construct 5 | Event 10 | RM38-1 | 0.24** | 0.3 | −1.93** |
| Construct 5 | Event 10 | RM34 | 0.07 | 0.27 | −2.6*** |
| Construct 5 | Event 10 | RM38-2 | 0.13 | 0.45 | −2.46*** |
| Construct 5 | Event 2 | RM38-1 | 0.24** | 0.3 | −1.48* |
| Construct 5 | Event 3 | RM38-1 | 0.24** | 0.32 | −1.85** |
| Construct 5 | Event 3 | RM34 | 0.07 | 0.29 | −2.52*** |
| Construct 5 | Event 3 | RM38-2 | 0.13 | 0.47* | −2.39*** |
| Construct 5 | Event 4 | RM38-1 | 0.24** | 0.3 | −2.14*** |
| Construct 5 | Event 4 | RM34 | 0.07 | 0.27 | −2.81*** |
| Construct 5 | Event 4 | RM38-2 | 0.13 | 0.45 | −2.67*** |
| Construct 5 | Event 5 | RM38-1 | 0.24** | 0.31 | −1.76** |
| Construct 5 | Event 5 | RM34 | 0.07 | 0.28 | −2.43*** |
| Construct 5 | Event 5 | RM38-2 | 0.13 | 0.46* | −2.29*** |
| Construct 5 | Event 6 | RM38-2 | 0.13 | 0.48* | −3.3*** |
| Construct 5 | Event 7 | RM38-1 | 0.24** | 0.33 | −2.2*** |
| Construct 5 | Event 7 | RM34 | 0.07 | 0.29 | −2.87*** |
| Construct 5 | Event 7 | RM38-2 | 0.13 | 0.48* | −2.73*** |
| Construct 5 | Event 8 | RM38-1 | 0.24** | 0.3 | −1.76** |
| Construct 5 | Event 8 | RM34 | 0.07 | 0.27 | −2.43*** |
| Construct 5 | Event 8 | RM38-2 | 0.13 | 0.45 | −2.29*** |
| Construct 5 | Event 9 | RM38-1 | 0.24** | 0.28 | −1.78** |
| Construct 5 | Event 9 | RM34 | 0.07 | 0.24 | −2.44*** |
| Construct 5 | Event 9 | RM38-2 | 0.13 | 0.43 | −2.31*** |

[1]Maturity = days from planting until 95% of pods within a plot are final mature color
[2]F2:3 bulk difference = (F2:3 positive bulk – F2:3 negative bulk)
*,,*significant at the 0.05, 0.01 and 0.001 level, respectively

Example 3: Corn Transgenic T x G Testing Utilizing the Association Mapping Method Association mapping was utilized in construct sorting. In Year1, constructs were transformed into a single isogenic testing background. For each construct, a set of 5-7 events were derived. Each event was blended into a balanced bulk by construct. Hybrid seed was produced by using the balanced bulks and the non-transgenic parent as females of F1 crosses. Each female was crossed to multiple inbred testers of the opposite heterotic group. Seeds from each construct were harvested and bulked as construct x tester combinations.

In Year2, the association mapping approach was tested with a drought tolerance construct, referred to hereafter as Construct 1. Five events of this construct were blended together in this experiment. The isogenic positive and null lines of Construct 1 were crossed to 127 testers of the opposite heterotic group which represent a wide variety of elite germplasm. The experiment was grown in Viluco, Chile utilizing 2 meter plots in drought stress (severe and moderate stress) and fully irrigated managements. Measurements of flowering time, plant stature, and photometry yield were taken in all locations. For each tester, a transgene positive and a transgene negative version were nested in side-by-side testing. The objective of the experiment was to detect a significant transgene main effect (T) and to quantify the size and significance of the transgene x germplasm interaction (TxG). Data were analyzed using the R analysis software package.

The growing degree units to silking (GDUSLK) phenotype were significantly increased in hybrids containing Construct 1 as compared to those lacking this transgene (Table 5). Construct 1 also significantly increased growing degree units to shedding (GDUSHD). However, the anthesis-silking interval (ASIGDU) effect of Construct 1 was not only small and insignificant, but inconsistent across environments. The association mapping method produced incredibly precise data for these flowering traits. In this example, a significant (p<0.001) but small (3.5 GDUSLK) effect was detected across germplasm for Construct 1. This incredibly high level of precision demonstrates the power of this method. In addition, a significant transgene by germplasm interaction for flowering time (Table 6) was also calculated, suggesting that the impact of Construct 1 on silking varies by genotype.

Plant height (PLTHT) and ear height (EARHT) was measured in these hybrids and detected that Construct 1 causes a significant reduction on both phenotypes (Table 5). In corn breeding, it is generally advantageous to produce plants with shorter stature and lower ear positioning that can maintain similar or greater yields. Construct 1 resulted in plants with the desired lower ears across environments. The impact of Construct 1 on PLTHT varied by environment. For example, in the flowering stress location PLTHT was reduced by 1.25 inches as a result of Construct 1, but PLTHT increased by 0.73 inches in the well-watered (WW) location. Significant transgene x environment and transgene x germplasm x environment (TxGxE) interaction were detected for this trait (Table 7). Transgene breeding values for PLTHT in different environmental conditions were evaluated. In the stress locations, there was no effect of the transgene on PLTHT, and this was consistent across families. Under WW (well-watered) conditions, some families had a significant increase in PLTHT, while others were neutral. This demonstrates strong TxGxE for Construct 2 for PLTHT.

The effect of Construct 1 on yield was also measured using ear photometry and combine yield. Construct 1 significantly reduced the total number of kernels set by almost 12 kernels per ear. This negative effect on kernel set resulted in lower yield by almost 11 bushels per acre. These negative trends in yield were found to be consistent across environments and germplasm. This indicates that Construct 1 did not produce the desired effect of increasing or stabilizing yield. The availability of this type of data early in advancement helps to prioritize constructs that produce desirable phenotypes over constructs that do not.

TABLE 5

Transgene Breeding Values (TBVs) for
Construct 1 using the Association
Mapping Method. Traits shown are yield
(in bushels/acre), GDUSHD (in heat units),
GDUSLK (in heat units), ASIGDU (in heat units),
EARHT (in inches), PLTHT (in inches), and
PHTKPE (in kernels per ear). TBVs that are statistically
significant at the p < .05 level are shown
in bold text.

| Trait | Loc | BLUP_Positive | BLUP_Negative | TBV | p_value |
|---|---|---|---|---|---|
| YIELD | Overall | 165 | 176 | −10.7 | <.001 |
| | GFS | 114 | 130 | −15.9 | <.001 |
| | FS | 119 | 126 | −7.31 | <.001 |
| | WW | 258 | 267 | −8.75 | <.001 |
| GDUSHD | Overall | 1182.7 | 1178.1 | 4.6 | 0.007 |
| | WW | 1202.6 | 1198.6 | 4 | 0.027 |
| | FS | 1170.1 | 1166 | 4.1 | 0.011 |
| | GFS | 1179 | 1173.5 | 5.5 | 0.012 |
| GDUSLK | Overall | 116.71 | 116.36 | 3.5 | <.001 |
| | GFS | 115.39 | 115.02 | 3.7 | 0.003 |
| | FS | 118.64 | 118.51 | 1.3 | 0.55 |
| | WW | 116.21 | 115.86 | 3.6 | 0.022 |
| ASIGDU | Overall | 73.3 | 73.43 | −0.13 | 0.93 |
| | GFS | 69.93 | 67.84 | 2.09 | 0.1 |
| | FS | 92.88 | 93.13 | −0.25 | 0.91 |
| | WW | 57.7 | 60.4 | −2.7 | 0.089 |
| EARHT | Overall | 54.04 | 54.69 | −0.65 | 0.003 |
| | GFS | 56.93 | 57.71 | −0.78 | 0.001 |
| | FS | 45.77 | 46.63 | −0.86 | 0.006 |
| | WW | 58.07 | 58.36 | −0.29 | 0.278 |

TABLE 5-continued

Transgene Breeding Values (TBVs) for
Construct 1 using the Association
Mapping Method. Traits shown are yield
(in bushels/acre), GDUSHD (in heat units),
GDUSLK (in heat units), ASIGDU (in heat units),
EARHT (in inches), PLTHT (in inches), and
PHTKPE (in kernels per ear). TBVs that are statistically
significant at the p < .05 level are shown
in bold text.

| Trait | Loc | BLUP_Positive | BLUP_Negative | TBV | p_value |
|---|---|---|---|---|---|
| PLTHT | Overall | 98.59 | 98.79 | −0.2 | <.001 |
| | GFS | 107.27 | 107.45 | −0.19 | 0.426 |
| | FS | 76.73 | 77.98 | −1.25 | <.001 |
| | WW | 109.09 | 108.36 | 0.73 | 0.278 |
| PHTKPE | Overall | 403.3 | 415.47 | −12.2 | 0.04 |
| | GFS | 349.15 | 373.07 | −23.9 | <.001 |
| | FS | 278.75 | 287.23 | −8.48 | 0.05 |
| | WW | 577.28 | 581.93 | −4.65 | 0.237 |

TABLE 6

Significant transgene x germplasm
interaction for GDUSLK with Construct 1.
The sources of variation for the construct
are shown in the chart, with the relevant p-values.
TxG is a statistically significant source of
variation, which means that the GDUSLK effect of
Construct 1 varies between testers. Var/SE(Var)
that are statistically significant are shown in bold text.

| Trait | Source | Var | Var/SE(Var) | p_value |
|---|---|---|---|---|
| GDUSLK | E | 11.32 | 0.91 | |
| GDUSLK | G | 1.75 | 6.52 | |
| GDUSLK | GxE | 0.02 | 0.37 | 0.71 |
| GDUSLK | TxE | 0 | 0 | 1 |
| GDUSLK | TxG | 0.13 | 1.86 | 0.03 |
| GDUSLK | TxGxE | 0 | 0 | 1 |

TABLE 7

Significant transgene x germplasm x environment
interaction for PLTHT with Construct 1.
The sources of variation for the
construct are shown in the chart, with the relevant
p-values. TxG is a statistically significant
source of variation, which means that the PLTHT
effect of Construct 1 varies with testers
and environments. Var/SE(Var) that are statistically
significant at the are shown in italicized/bold text.

| Trait | Source | Var | Var/SE(Var) | p_value |
|---|---|---|---|---|
| PLTHT | E | 290.5 | 0.99 | |
| PLTHT | G | 3.03 | 5.86 | |
| PLTHT | GxE | 0.64 | *2.51* | 0 |
| PLTHT | TxE | 0.44 | *1.03* | 0 |
| PLTHT | TxG | 0.2 | *1.45* | 0 |
| PLTHT | TxGxE | 0.45 | *2.04* | 0.02 |

Additional experiments using the association mapping method show that it is possible to detect significant main T, TxG, TxE, and TxGxE interactions for plant establishment, standability, and physiological framework phenotypes. With this association mapping data, it is also possible to predict the effect of the tested construct across related germplasm without having to test the effect empirically. Based on association mapping methods, it is possible to predict how consistently these constructs would contribute positively to other elite material. The association mapping method provides a rapid technique to quantify TxG and the general combining ability (GCA) of early stage constructs.

Example 4: Corn T x G Testing Utilizing the Double Haploid Method

Double haploids are utilized routinely in breeding of corn and other crops. The double haploid method has been adapted to allow constructs of interest to segregate in populations. These populations can then be used to estimate the breeding value of the construct in diverse germplasm.

Double haploid (DH) populations were created by crossing a line carrying Construct 2 for drought tolerance to multiple elite lines to produce F1s. Double haploids were generated from these F1s. DHs were top-crossed to a single tester from the opposite heterotic group. Hybrids derived from this top-cross were yield tested in a number of locations and environments in Chile and North America. Numerous phenotypes, including flowering time, plant stature, and yield related phenotypes were measured. Also, each double haploid line was analyzed for a standard set of ~100 SNP markers (Table 8). In the stress locations, families tended to respond positively to the presence of Construct 2, and sometimes significantly. Under WW conditions, some families were positively impacted for yield while other showed significant losses. This demonstrates strong TxGxE for Construct 2 for yield.

irrigated environments (Table 7). This suggests that Construct 2 can behave quite differently when placed in different genetic and physical environments. This is similar to what was observed for yield for this transgene (Table 8). In certain environments and in certain families, Construct 2 had a strong positive effect on yield. However, this effect was reversed in other families and environments.

Phenotypic data generated from the double haploids were used to create an estimation dataset. Combining these data with the molecular marker data using association models in the BT-SAT software allowed us to predict the effect of Construct 2 in a wide variety of elite and untested germplasm Using the drop-pop method, the efficiency of using this technique to predict the specific combining ability (SCA) and GCA of Construct 2 was validated (FIG. 3).

The isoline method is a rapid way to identify if a transgene may have an effect on agronomic traits such as emergence, maturity, and yield. However, there may be unknown somoclonal and epigenetic effects from the transformation process that may be present in transgene positive isolines that can skew agronomic performance data. Also, isoline testing can inaccurately estimate the general combining ability of transgenes across germplasm if there is significant transgene x germplasm interaction. Utilizing the techniques of F2:3s, association mapping, and double haploids in combination with isoline testing can enable better decision-

TABLE 8

Number of Double Haploid Lines per population and their transgene breeding values (TBV) for each trait. TBVs that are significantly greater than 0 are in bold text. There are differences among populations for TBVs for some traits but not for others.

| Population | # of Lines | ASIGDU | EARHT | GDUSHD | GDUSLK | MST | PLTHT | Yield |
|---|---|---|---|---|---|---|---|---|
| All Pops | 1237 | -1.76 | 0.1 | 0.41 | 0.23 | -0.1 | 0.18 | 1.21 |
| A x B | 147 | -1.76 | 0.1 | -0.03 | 0.22 | -0.43 | 0.18 | -0.49 |
| A x C | 169 | -1.77 | 0.11 | 0.59 | 0.23 | -0.07 | 0.19 | 1.03 |
| A x D | 186 | -1.76 | 0.1 | 0.62 | 0.22 | 0.06 | 0.18 | 0.62 |
| A x E | 49 | -1.76 | 0.11 | 0.22 | 0.22 | -0.15 | 0.18 | 1.05 |
| A x F | 169 | -1.77 | 0.1 | 0.27 | 0.22 | -0.26 | 0.18 | -0.21 |
| A x G | 171 | -1.76 | 0.1 | 0.38 | 0.22 | -0.02 | 0.18 | 1.91 |
| A x H | 189 | -1.76 | 0.1 | 0.52 | 0.23 | 0.25 | 0.18 | 3.92 |
| A x I | 157 | -1.76 | 0.1 | 0.67 | 0.22 | -0.2 | 0.18 | 1.86 |

The phenotypic data were analyzed using both a strictly additive model and an interactive model. These data were used to estimate a transgene breeding value (TBV) for each construct. These values were derived for all of the phenotypes measured. In addition, the size of the transgene x family interaction was used as a measure of the size of the non-additive interactions between the construct and native diversity. Further, the effect of adding the transgene to a set of untested germplasm was predicted using scripts in the BT-SAT analysis software package.

Small but significant (p<0.05) effects of Construct 2 on germplasm could be detected using the DH method. For example, Construct 2 significantly and subtly increased GDUSHD by 4 GDUs and reduced the anthesis-silking interval (ASIGDU) by 1.8 GDUs (approximately 2 hours) (Table 4X). Although the average effect on flowering time was small, it was quite consistent across environments and families.

A significant main effect of Construct 2 on PLTHT or EARHT (Table 8) was not detected. However, a strong transgene by family by environment interaction for PLTHT was seen, where the PLTHT effect was non-evident in stress conditions, but present in certain backgrounds under fully making of which transgenes and genome edits to advance for further testing and potential registration and commercialization.

Example 5: Corn Transgenic T by G Testing Utilizing the Different Filial and Backcrossing Generations In 'bi-parental' breeding crosses, $T_0$ plant of every event is crossed with 4-5 or more elite inbred lines in its respective heterotic group. Resulting $F_1$'s are selfed to generate $F_{2:3}$'s and/or $F_3$'s bulk populations for first year field trials. Selected $F_{2:3}$'s and/or $F_3$'s homozygous and null segregants are used for first year trials; whereas the selected hemizygous segregant from the same populations is further selfed to derive recombinant inbred lines (RILs) ($F_4$ to $F_n$ generation) using a single seed descent approach. In the $F_5$ or $F_6$ generation, the hemizygous RILs are selfed and respective homozygous and null segregants are selected for consecutive year trials. In 'unfinished' backcrosses, backcross populations are developed without the use of marker-assisted backcrossing. Random selection of backcross plants with population sizes of 5-10 plants/generation would be used.

The selection done in each generation would be for the introgressed event, significantly lowering the backcrossing costs. $BC_2F_2$ plants or $BC_3F_2$ homozygous plants would be used for inbred and hybrid testing. The bi-parental breeding crosses approach along with 'unfinished' conversions provide a path toward lower cost TxG testing, with adequate resolution to detect TxG effects. Using appropriate experimental design, the generated RILs can also be used to derive estimation sets for predicting the performance of transgene or a genome edit in untested germplasm.

Below is an example of how 'bi-parental' breeding crosses are utilized in transgenic event sorting for insect protection traits.

Figure 4:
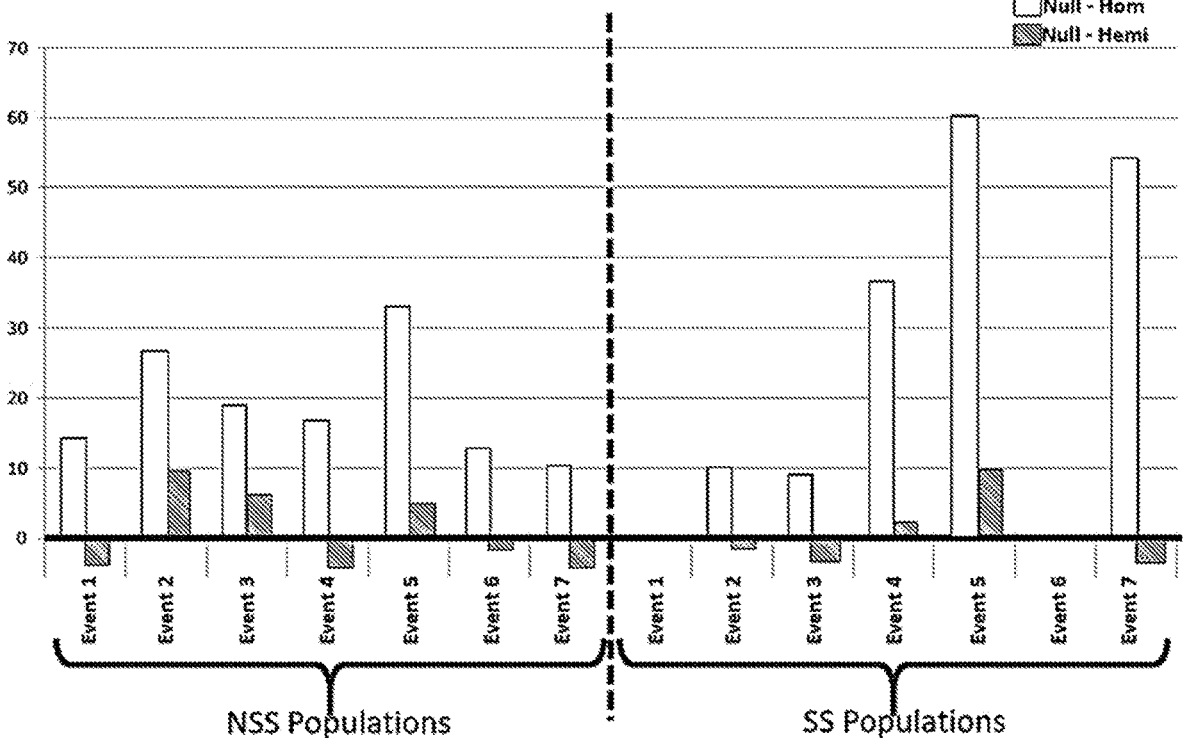
FIG. 4 shows estimated yield differences (bu/ac) of Null vs Homozygous (Hom) and Null vs Hemizygous segregant of different transgenic events in non-stiff stalk (NSS) and stiff stalk (SS) $F_2$ populations.

In Year1, events from different traits in same direct or conversion backgrounds were crossed with multiple elite inbred lines in their respective heterotic groups. Resulting $F_2$ populations were planted in two locations in North America in Year2. The segregating $F_2$ populations were sampled for zygosity analysis and Homozygous/Hemizygous/Null segregants were tagged in the field for general observations throughout the growing season along with getting the yield estimates using ear photometry. FIG. 4 demonstrates the yield difference of Null minus the homozygous (hom) and hemizygous (hemi) $F_2$ segregant in NSS and SS populations for 7 transgenic events. Overall, 7 events showed different level of yield drag when hom was compared with null and it seemed to be varied among the different populations. For example, event 5 had on average −45 bu/ac yield drag across populations; with ~32 in NSS and ~60 bu/ac drag in SS population. Whereas, event 7 had ~54 bu/ac in SS and only ~10 bu/ac drag in NSS populations. The yield drag was observed more in the hom compared to the hemizygous segregants. For example, in the case of event 5 and 7 where in hom it showed a drag of 60 and 54 bu/ac in SS populations; the respective hemi segregant showed ~10 bu/ac in event 5 to no drag in event 7.

Based on $F_2$ results, 5 of 7 events were advanced to $F_3$ stage for further analysis in year Year3. For $F_3$ populations, the 5 events in the same three conversion backgrounds were crossed with multiple elite inbreds. Balanced bulk of homozygous and null segregants were made and planted in two locations in North America. During the growing season general observations were made and yield estimates were done using ear photometry.

Figure 5:
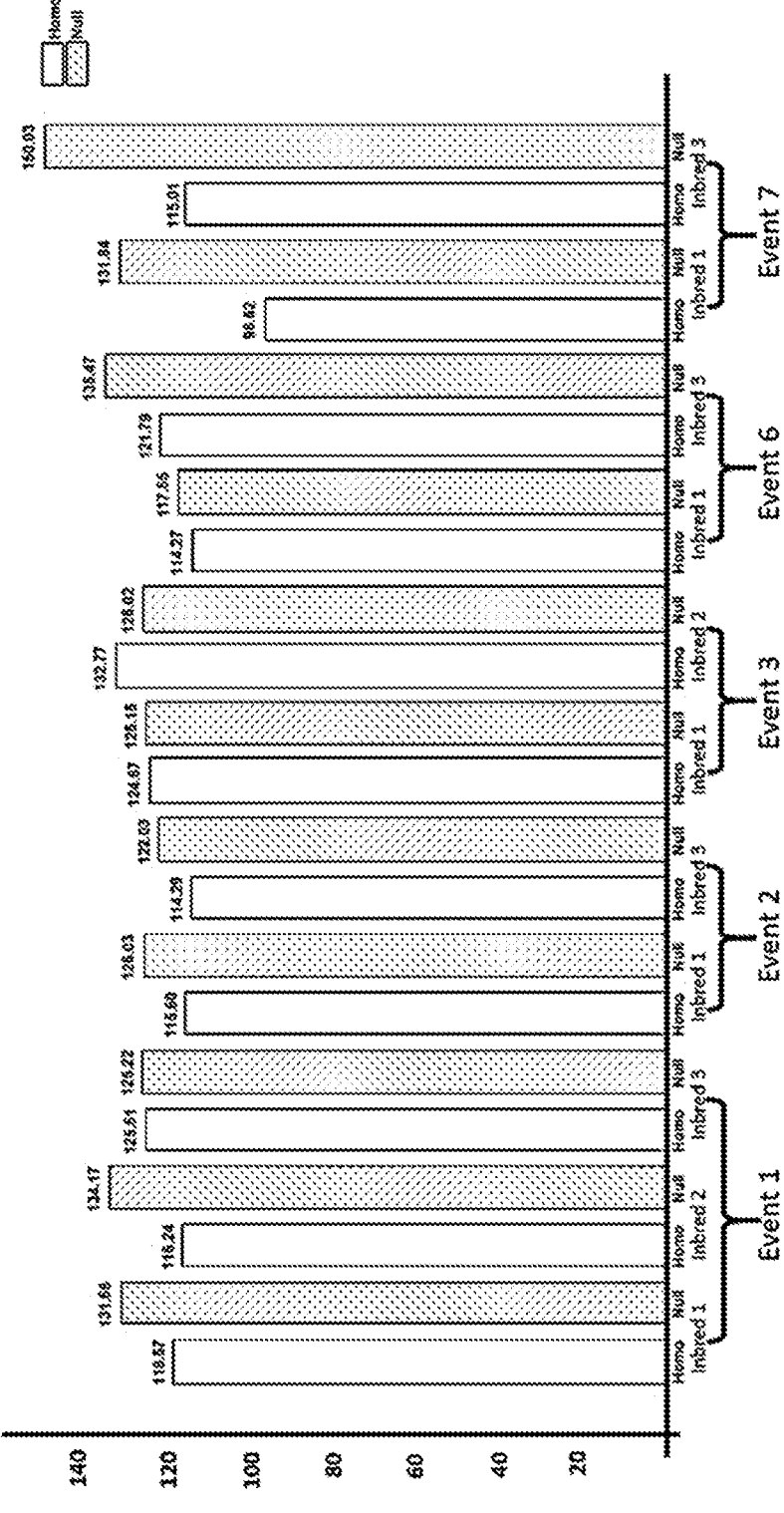
FIG. 5 shows breeding value comparisons for homozygous transgenic events and homozygous null (no transgene) in the same genetic background using F3 bulk populations.

In $F_3$ populations the observed estimate of transgene (T) impact was confirmed with overall negative impact of the transgene on inbred yield and it varied among the background (FIG. 5). Event 1 had significant impact on yield in families generated from Inbred 1 and 2; whereas $F_3$ families in Inbred 3 did not have significant impact on the yield when homozygous were compared with respective null families. Lesser in magnitude but similar trend was observed in Event 6 as well, with more yield drag in families from inbred 3 compared to inbred 1 family. Event 7 had significant and very similar 'T' impact across families from both inbred backgrounds. Overall event 3 performed the best within and across families.

The effect of insect protection traits on yield was measured using ear photometry using $F_2$ and $F_3$ families and the majority of the events had significantly reduced the yield in homozygous state and the effect varied by the background. Having this data available during early stages of construct and events sorting can help estimate the overall 'T' impact along with 'GxT' interactions on the event basis, which allows sorting of the events that have minimal to no negative agronomic effects over those that do in transgene characterization and development process.

That which is claimed:

1. A method for accelerated selection of a genome edited plant comprising at least five site-specific genome edits introduced via CRISPR/Cas, wherein said site-specific genome edits comprise targeted mutagenesis and do not comprise stable integration of exogenous polynucleotides, the method comprising:

(a) crossing a plant line or a population of plants that is homozygous positive for the genome edits with a diverse panel of plant lines that do not contain said genome edits;

(b) crossing an isogenic null of (a) with the same diverse panel of plant lines of (a) that do not contain said genome edits, wherein the isogenic null of (a) is homozygous negative for the genome edits;

(c) collecting segregating offspring of said crosses of (a) and (b) to produce a bulk pool of genome edits positive and genome edits negative hybrids;

(d) phenotyping or genotyping the bulk pool of hybrids that are positive for the genome edits and the hybrids that are negative for the genome edits;

(e) assigning a breeding value to each genome edited plant or a subset of the genome edits in the genome edited hybrids based on the phenotyping or the genotyping; and (f) selecting the genome edits based on the breeding value.

2. The method of claim 1, further comprising growing the positive and negative hybrids in adjacent yield plots having similar environmental conditions.

3. The method of claim 2, further comprising comparing agronomic characteristics of said positive and negative plant.

4. The method of claim 3, wherein the agronomic characteristics are selected from the group consisting of emergence, early vigor, growth, flowering time, flowering duration, height, maturity, and yield.

5. The method of claim 1, wherein whole genome molecular markers are used to characterize the hybrid plants.

6. The method of claim 1, wherein whole genome marker by genome edits is used to predict a win/loss and genome edit breeding value of said genome edits.

7. The method of claim 3, further comprising setting a criterion for acceptable agronomic phenotype.

8. The method of claim 1, wherein the breeding value is assigned based on both phenotyping and genotyping.

* * * * *